US012661411B2

(12) United States Patent
Bollyky et al.

(10) Patent No.: US 12,661,411 B2
(45) Date of Patent: Jun. 23, 2026

(54) MONOCLONAL ANTIBODY AND VACCINE TARGETING FILAMENTOUS BACTERIOPHAGE

(71) Applicant: INIMMUNE CORPORATION, Missoula, MT (US)

(72) Inventors: Paul L. Bollyky, Stanford, CA (US); William Parks, Seattle, WA (US); Patrick Secor, Seattle, WA (US)

(73) Assignee: Inimmune Corp., Missoula, MT (US)

( * ) Notice: Subject to any disclaimer, the term of this patent is extended or adjusted under 35 U.S.C. 154(b) by 0 days.

(21) Appl. No.: 18/425,772

(22) Filed: Jan. 29, 2024

(65) Prior Publication Data

US 2024/0350634 A1     Oct. 24, 2024

Related U.S. Application Data

(63) Continuation of application No. 17/066,005, filed on Oct. 8, 2020, now Pat. No. 11,911,472, which is a continuation of application No. 16/262,548, filed on Jan. 30, 2019, now Pat. No. 10,835,607, which is a continuation of application No. 15/219,073, filed on Jul. 25, 2016, now abandoned.

(60) Provisional application No. 62/196,147, filed on Jul. 23, 2015.

(51) Int. Cl.
| | |
|---|---|
| *A61K 39/104* | (2006.01) |
| *A61K 39/00* | (2006.01) |
| *A61K 47/64* | (2017.01) |
| *C07K 16/08* | (2006.01) |
| *C07K 16/1214* | (2026.01) |

(52) U.S. Cl.
CPC .......... *A61K 47/646* (2017.08); *A61K 39/104* (2013.01); *C07K 16/08* (2013.01); *C07K 16/1214* (2013.01); *A61K 39/00* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | |
|---|---|---|
| 10,835,607 B2 | 11/2020 | Bollyky et al. |
| 2003/0113742 A1 | 6/2003 | Whiteley et al. |

FOREIGN PATENT DOCUMENTS

| | | |
|---|---|---|
| WO | WO 2008/094942 A2 | 8/2008 |
| WO | WO 2009/064854 A2 | 5/2009 |
| WO | WO 2011/111180 A1 | 9/2010 |

OTHER PUBLICATIONS

Lloyd et al. Protein Engineering, Design & Selection 22: 159-168, 2009.*
Asakura et al. Interaction between Particles Suspended in Solutions of Macromolecules. J Polym Sci 33:183-192 (1958).
Boulanger. Purification of bacteriophages and SOS-PAGE analysis of phage structural proteins from ghost particles. Methods Mol Biol 502:227-238 (2009).
Brandt et al. DNA concentration and length in sputum of patients with cystic fibrosis during inhalation with recombinant human DNase. Thorax 50:880-882 (1995).
Castang, S. et al. (2012) "Basis for the Essentiality of H-NS Family Members in Pseudomonas aeruginosa," J Bacterial. 194(18):5101-5109.
Chang et al. Alginate production by Pseudomonas putida creates a hydrated microenvironment and contributes to biofilm architecture and stress tolerance under water-limiting conditions. J Bacterial 189:8290-8299 (2007).
Costerton, J.W. et al. (1999) "Bacterial Biofilms: A Common Cause of Persistent Infections," Science 284(5418):1318-1322.
Dogic et al. Elongation and fluctuations of semiflexible polymers in a nematic solvent. Phys Rev Lett 92:125503 (2004).
Dogic et al. Ordered phases of filamentous viruses. Curr Opin Colloid In 11 :47-55 (2006).
Finnan et al. Genome diversity of Pseudomonas aeruginosa isolates from cystic fibrosis patients and the hospital environment. J Clin Microbial 42:5783-5792 (2004).
Folsom et al. Physiology of Pseudomonas aeruginosa in biofilms as revealed by transcriptome analysis. BMC Microbial 10:294 (2010).
Fothergill et al. Transmissible strains of Pseudomonas aeruginosa in cystic fibrosis lung infections. Eur Respir J 40:227-238 (2012).
Gill et al. Proteoglycans: key regulators of pulmonary inflammation and the innate immune response to lung infection. Anat Rec (Hoboken) 293:968-981 (2010).
Glazer et al. An automatic optical imaging system for birefringent media. Pro R Soc Lond A 452:2751-2765 (1996).
Häußler. Biofilm formation by the small colony variant phenotype of Pseudomonas aeruginosa. Environ Microbial 6:546-551 (2004).
Hentzer et al. Transcriptome analysis of Pseudomonas aeruginosa biofilm development: anaerobic respiration and iron limitation. Biofilms 2:37-61 (2005).
Hoang et al. A broad-host-range Flp-FRT recombination system for site-specific excision of chromosomally-located DNA sequences: application for isolation of unmarked Pseudomonas aeruginosa mutants. Gene 212:77-86 (1998).
Høby et al. Pseudomonas aeruginosa biofilms in cystic fibrosis. Future Microbial 5:1663-1674 (2010).
Hood et al. A type VI secretion system of Pseudomonas aeruginosa targets a toxin to bacteria. Cell Host Microbe 7:25-37 (2010).

(Continued)

*Primary Examiner* — S. Devi
(74) *Attorney, Agent, or Firm* — Michael Best & Friedrich LLP

(57) ABSTRACT

Described here is a method for reducing or preventing *Pseudomonas aeruginosa* biofilm formation in a human subject in need thereof, comprising administering to the human subject a first composition comprising (a) an antigen-binding polypeptide that binds Pf-family bacteriophage, or (b) a vaccine against Pf-family bacteriophage. Also described is an antigen-binding polypeptide that binds specifically to a CoaB protein of Pf-family bacteriophage or fragment thereof.

2 Claims, 13 Drawing Sheets

Specification includes a Sequence Listing.

(56)             References Cited

OTHER PUBLICATIONS

Hunt et al. Macromolecular mechanisms of sputum inhibition of tobramycin activity. Antimicrob Agents Chemother 39:34-39 (1995).

Jarvis. Benchmarking for prevention: the Centers for Disease Control and Prevention's National Nosocomial Infections Surveillance (NNIS) system experience. Infection 31 Suppl 2:44-48 (2003).

Jones et al. Identification of airborne dissemination of epidemic multiresistant strains of Pseudomonas aeruginosa at a CF centre during a cross infection outbreak. Thorax 58:525-527 (2003).

Kirov et al. Biofilm differentiation and dispersal in mucoid Pseudomonas aeruginosa isolates from patients with cystic fibrosis. Microbiology 153:3264-327 4 (2007).

Manos et al. Transcriptome analyses and biofilm-forming characteristics of a clonal Pseudomonas aeruginosa from the cystic fibrosis lung. J Med Microbiol 57:1454-1465 (2008).

Mathee et al. Dynamics of Pseudomonas aeruginosa genome evolution. PNAS USA 105:3100-3105 (2008).

Matsui et al. A physical linkage between cystic fibrosis airway surface dehydration and Pseudomonas aeruginosa biofilms. PNAS USA 103:18131-18136 (2006).

Mcelroy et al. Strain-specific parallel evolution drives short-term diversification during Pseudomonas aeruginosa biofilm formation. PNAS USA 111:E1419-1427 (2014).

Mooij et al. Characterization of the integrated filamentous phage Pf5 and its involvement in small-colony formation. Microbiology 153:1790-1798 (2007).

Onsager. The effects of shape on the interaction of colloidal particles. Ann NY Acad Sci 51:627-659 (1949).

Ophir et al. A role for exopolysaccharides in the protection of microorganisms from desiccation. Appl Environ Microbiol 60:740-745 (1994).

Panagea et al. Environmental contamination with an epidemic strain of Pseudomonas aeruginosa in a Liverpool cystic fibrosis centre, and study of its survival on dry surfaces. J Hosp Infect 59:102-107 (2005).

Parsley et al. Identification of diverse antimicrobial resistance determinants carried on bacterial, plasmid, or viral metagenomes from an activated sludge microbial assemblage. Appl Environ Microbial 76:3753-3757 (2010).

Petrova et al. The novel Pseudomonas aeruginosa two-component regulator BfmR controls bacteriophage-mediated lysis and DNA release during biofilm development through PhdA. Mol Microbial 81 :767-783 (2011 ).

Platt et al. Proteomic, microarray, and signature-tagged mutagenesis analyses of anaerobic Pseudomonas aeruginosa at pH 6.5, likely representing chronic, late-stage cystic fibrosis airway conditions. J Bacterial 190:2739-2758 (2008).

Poon. The physics of a model colloid-polymer mixture. J Phys-Condens Mat 14:R859-R880 (2002).

Rakonjac et al. Filamentous Bacteriophage: Biology, Phage Display and Nanotechnology Applications. Curr Issues Mol Biol 13:51-76 (2011).

Rice, S.A. et al. (2009) "The biofilm life cycle and virulence of Pseudomonas aeruginosa are dependent on a filamentous prophage," The ISME Journal 3:271-282.

Schmidt et al. Viscoelastic properties of semiflexible filamentous bacteriophage fd. Phys Rev E Stat Phys Plasmas Fluids Relat Interdiscip Topics 62:5509-5517 (2000).

Schulz et al. Cystic fibrosis transmembrane conductance regulator can export hyaluronan. Pathobiology 77:200-209 (2010).

Secor, P.R. et al. (2015) "Filamentous Bacteriophage Promote Biofilm Assembly and Function," Cell Host & Microbe 18:549-559.

Shak et al. Recombinant human DNase I reduces the viscosity of cystic fibrosis sputum. PNAS USA 87:9188-9192 (1990).

Stewart, P.S. (2002) "Mechanisms of antibiotic resistance in bacterial biofilms," Int J Med Microbial. 292(2):107-113.

Tseng et al. The extracellular matrix protects Pseudomonas aeruginosa biofilms by limiting the penetration of tobramycin. Environ Microbial 15:2865-2878 (2013).

Vasconcellos et al. Reduction in viscosity of cystic fibrosis sputum in vitro by gelsolin. Science 263:969-971 (1994).

Waldor et al. Lysogenic conversion by a filamentous phage encoding cholera toxin. Science 272:1910-1914 (1996).

Walters et al. Contributions of antibiotic penetration, oxygen limitation, and low metabolic activity to tolerance of Pseudomonas aeruginosa biofilms to ciprofloxacin and tobramycin. Antimicrob Agents Chemother 47:317-323 (2003).

Webb et al. Cell death in Pseudomonas aeruginosa biofilm development. J Bacterial 185:4585-4592 (2003).

Webb, J.S. et al. (2004) "Bacteriophage and Phenotypic Variation in Pseudomonas aeruginosa Biofilm Development," J. Bacterial. 186(23):8066-8073.

Whitchurch et al. Extracellular DNA required for bacterial biofilm formation. Science 295:1487 (2002).

Whiteley et al. Gene expression in Pseudomonas aeruginosa biofilms. Nature 413:860-864 (2001).

Winstanley et al. Newly introduced genomic prophage islands are critical determinants of in vivo competitiveness in the Liverpool Epidemic Strain of Pseudomonas aeruginosa. Genome Res 19:12-23 (2009).

Wnorowska et al. Bactericidal activity of cathelicidin LL-37 and select cationic lipids against the hypervirulent P. aeruginosa strain LESB58. Antimicrob Agents Chemother 59(7):3808-3815 (2015).

Yeung et al. Swarming of Pseudomonas aeruginosa is controlled by a broad spectrum of transcriptional regulators, including MetR. J Bacterial 191 :5592-5602 (2009).

Yokoyama, WM. et al. (2013) "Production of Monoclonal Antibodies," Current Protocols in Immunology 102: II :2.5:2.5.1-2.5.29.

Zhao et al. Psl trails guide exploration and microcolony formation in Pseudomonas aeruginosa biofilms. Nature 497:388-391 (2013).

* cited by examiner

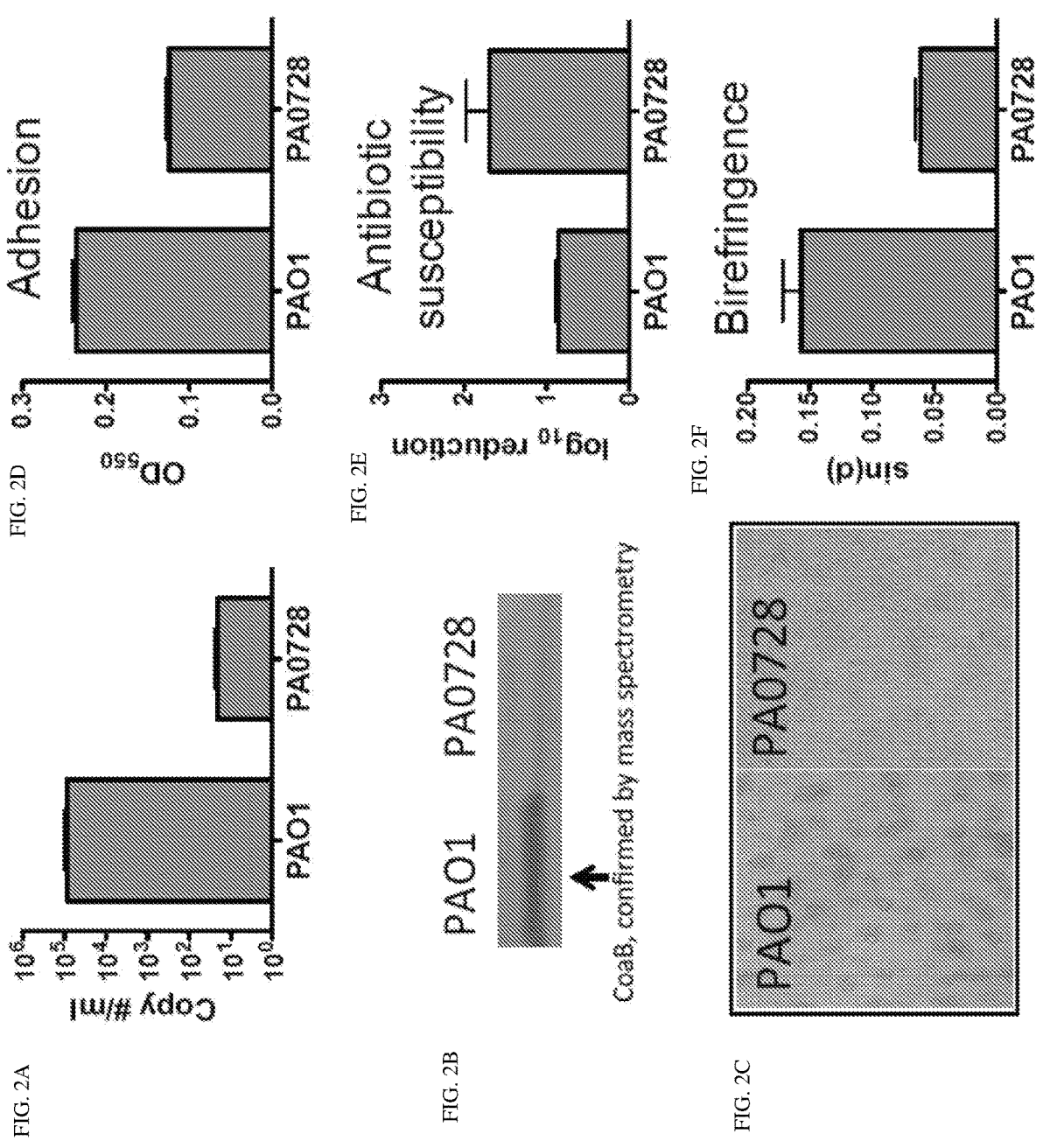

MONOCLONAL ANTIBODY AND VACCINE TARGETING FILAMENTOUS BACTERIOPHAGE

CROSS-REFERENCE TO RELATED APPLICATIONS

This application is a continuation of U.S. patent application Ser. No. 17/066,005, filed Oct. 8, 2020, now U.S. Pat. No. 11,911,472, which is a continuation of U.S. patent application Ser. No. 16/262,548, filed on Jan. 30, 2019, now U.S. Pat. No. 10,835,607, which is a continuation of U.S. patent application Ser. No. 15/219,073, filed on Jul. 25, 2016, now abandoned, which claims the benefit of U.S. Provisional Patent Application No. 62/196,147, filed on Jul. 23, 2015, the entire contents of each of which are fully incorporated herein by reference.

FEDERAL FUNDING STATEMENT

This invention was made with Government support under contract HL007287 awarded by the National Institutes of Health. The Government has certain rights in the invention.

SEQUENCE LISTING

This application was filed with a Sequence Listing in ST.26 XML format accordance with 37 C.F.R. § 1.831 and PCT Rule 13ter. The Sequence Listing XML file submitted in the USPTO Patent Center, "210468-9004-US03_sequence_listing_XML_9 Jul. 2024.xml," was created on Jul. 9, 2024, contains 31 sequences, has a file size of 28.0 kilobytes (28,672 bytes), and is incorporated by reference in its entirety into the specification.

BACKGROUND

*Pseudomonas aeruginosa* is an opportunistic pathogen in multiple clinical settings, including devastating pulmonary infections in individuals with the genetic disorder cystic fibrosis (CF). The virulence of *P. aeruginosa* is predicated on its ability to form biofilms, which are organized communities of bacteria encased in a polymer-rich matrix. Bacterial biofilms are ubiquitous in nature, and they endow bacteria with the ability to resist antibiotics and evade host immune defense mechanisms. See Costerton et al., *Science* 284:1318 (1999); Stewart et al., Int. *J. Med. Microbiol.* 292:107 (2002).

Thus, a need exists to develop therapeutic agents that can inhibit the formation of *P. aeruginosa* biofilms thereby making *P. aeruginosa* infections more susceptible to antibiotic treatment.

SUMMARY

Many embodiments described herein relate to a method for reducing or preventing *P. aeruginosa* biofilm formation in a human subject in need thereof, comprising administering to the human subject a first composition comprising (a) an antigen-binding polypeptide that binds Pf-family bacteriophage, or (b) a vaccine against Pf-family bacteriophage.

In one embodiment, the first composition comprises an antigen-binding polypeptide. In one embodiment, the antigen-binding polypeptide binds specifically to a CoaB protein of Pf-family bacteriophage or fragment thereof. In one embodiment, the antigen-binding polypeptide is IgG or IgM.

In one embodiment, the first composition further comprises an antibiotic, or the method further comprises administering a second composition comprising an antibiotic to the human subject.

In one embodiment, the human subject is infected with a *P. aeruginosa* strain resistant to one or more antibiotics.

In one embodiment, the first composition comprises a vaccine against Pf-family bacteriophage. In one embodiment, the vaccine comprises an immunogenic fragment of Pf-family bacteriophage.

In one embodiment, the CoaB protein or fragment thereof comprises the amino acid sequence of GVIDTSAVE-SAITDGQGDM (SEQ ID NO: 1).

In one embodiment, the human subject is suffering from cystic fibrosis, burns, chronic would, chronic rhinosinusitis, ventilator-associated pneumonia, catheter-associated urinary tract infections, septic shock, and/or gastrointestinal infections.

Further embodiments described herein relate to an antigen-binding polypeptide that binds specifically to a CoaB protein of Pf-family bacteriophage or fragment thereof.

In one embodiment, the antigen-binding polypeptide specifically binds to an antigenic fragment of the CoaB protein comprising the amino acid sequence of GVIDTSAVE-SAITDGQGDM (SEQ ID NO: 1).

In one embodiment, the antigen-binding polypeptide is a monoclonal antibody, a chimeric antibody, a humanized antibody, a Fab fragment, a Fab' fragment, a F(ab')2 fragment, or an scFv molecule. In one embodiment, the antigen-binding polypeptide is IgG or IgM.

Another embodiment described herein relates to a pharmaceutical composition comprising (a) the antigen-binding polypeptide described herein or a fusion molecule comprising the antigen-binding polypeptide, and (b) a pharmaceutically acceptable carrier.

Another embodiment described herein relates to a polynucleotide encoding the antigen-binding polypeptide described herein.

Another embodiment described herein relates to an expression cassette comprising a promoter operably linked to the polynucleotide described herein.

Another embodiment described herein relates to a vector comprising the expression cassette described herein.

Another embodiment described herein relates to a transformed cell comprising the expression cassette or the vector described herein.

Another embodiment described herein relates to a method for producing an antigen-binding polypeptide, comprising culturing the transformed cell described herein, and isolating the antigen-binding polypeptide expressed by the transformed cell.

In one embodiment, the methods herein relate to the co-delivery of antibiotics with the antigen-binding polypeptide (e.g., monoclonal antibody) described herein.

Additional embodiments described herein relate to a vaccine against Pf-family bacteriophage, comprising (a) an immunogenic fragment of CoaB protein of Pf-family bacteriophage, and (b) a pharmaceutically acceptable excipient.

In one embodiment, the immunogenic fragment of CoaB protein consists of the amino acid sequence of GVIDT-SAVESAITDGQGDM (SEQ ID NO:1)

These and other features, together with the organization and manner of operation thereof, will become apparent from the following detailed description when taken in conjunction with the accompanying drawings.

BRIEF DESCRIPTION OF THE DRAWINGS

FIG. 1A: Pf4 production by colony biofilms formed from the indicated strains enumerated as plaque forming units/milliliter (PFU/ml). Two versions of the standard PA01 *P. aeruginosa* lab strain were used: a "rough" strain that produces only a modest biofilm and a small colony variant (SCV) strain that produces robust biofilms. In addition, strain PA0728, a version of PA01 that does not produce Pf phage, was also used. Adjusted total Pf phage content are also plotted on the right axis. Results are mean±SD of three experiments. FIG. 1C: Birefringence (sin(d)) of the indicated colony biofilms was quantified after normalizing for sample thickness. Birefringence, the capacity of a material to split light into two beams with perpendicular polarization, is a signature characteristic of crystals, Thus, assessments of birefringence can be used to determine whether a biofilm is a crystal. Birefringence was again measured after washing of the bacteria to remove the extracellular matrix. Results are mean±SD of four experiments. FIG. 1D: Representative images for SVC and "rough" colony biofilms (placed between glass plates) visualized through crossed polarizing lenses. Birefringence is visualized as bright areas where light passes through both polarizing lenses. The birefringence patterns change when the sample is rotated with respect to the polarizing lenses, revealing extended areas of birefringence. Together, the data in FIG. 1A-1D show that biofilms made by *P. aeruginosa* are liquid crystals and that this crystalline organization is dependent on the presence of Pf phage.

FIG. 2A-2F show that a filamentous bacteriophage, Pf4, contributes to *P. aeruginosa* biofilm function. FIG. 2A-2F show data describing biofilm characteristics for two strains of *P. aeruginosa*-PA01 (a standard laboratory strain) and PA0728 (a version of PA01 from which the promoter responsible for Pf4 phage production has been deleted, such that Pf phage production is reduced). In FIG. 2A, the Pf phage copy number is shown for *P. aeruginosa* strains PA01 and PA0728, as measured by quantitative PCR. In FIG. 2B the amount of CoaB protein, the coat protein that surrounds phage, is shown to be reduced in PA0728 versus PA01 by Mass Spectrometry. In FIG. 2C, the amount of *P. aeruginosa* colony aggregation is shown to be reduced for PA0728 versus PA01. In FIG. 2D, the adhesion of these bacterial colonies is shown for PA0728 versus PA01, as measured in a flow chamber and crystal violet staining. In FIG. 2E, the susceptibility of PA0728 versus PA01 to 10 µg/ml of the antibiotic gentamycin is shown. In FIG. 2F, the birefringence of PA0728 versus PA01 is shown. It has been recently reported that Pf phage contribute to the organization of *P. aeruginosa* biofilms into a liquid crystal and that this contributes to biofilm adhesion and antibiotic tolerance. Together, the data in FIG. 2A-2F show that the presence of Pf phage contributes to *P. aeruginosa* biofilm function. These data are further elaborated upon in Secor et al., Cell Host & Microbe., 18(5):549-559 (2015).

Figure 5:
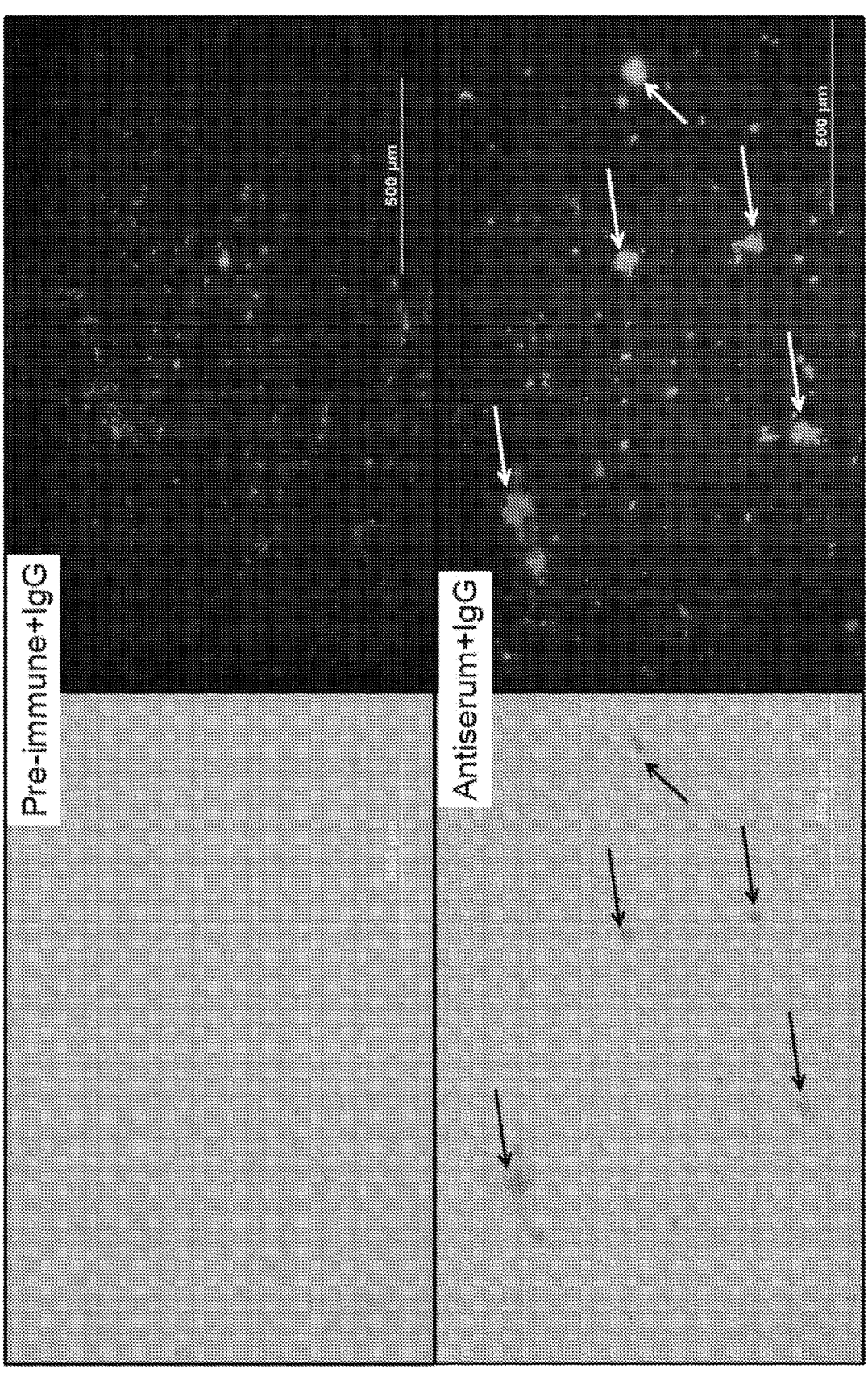

FIG. 5 shows that the addition of secondary antibodies (IgG) to biofilms pre-treated with antiserum undergo aggregation and clumping. Serum from rabbits before (pre-serum) or after immunization against Pf4 phage (anti-serum) was added to cultures of a strain of PA01. Then, a fluorescently labeled secondary antibody against rabbit IgG was used to visualize the clustering of bacteria. Confocal microscopy images are shown on the Left side of the image while fluorescence microscopy images are shown on the Right.

Figure 6:
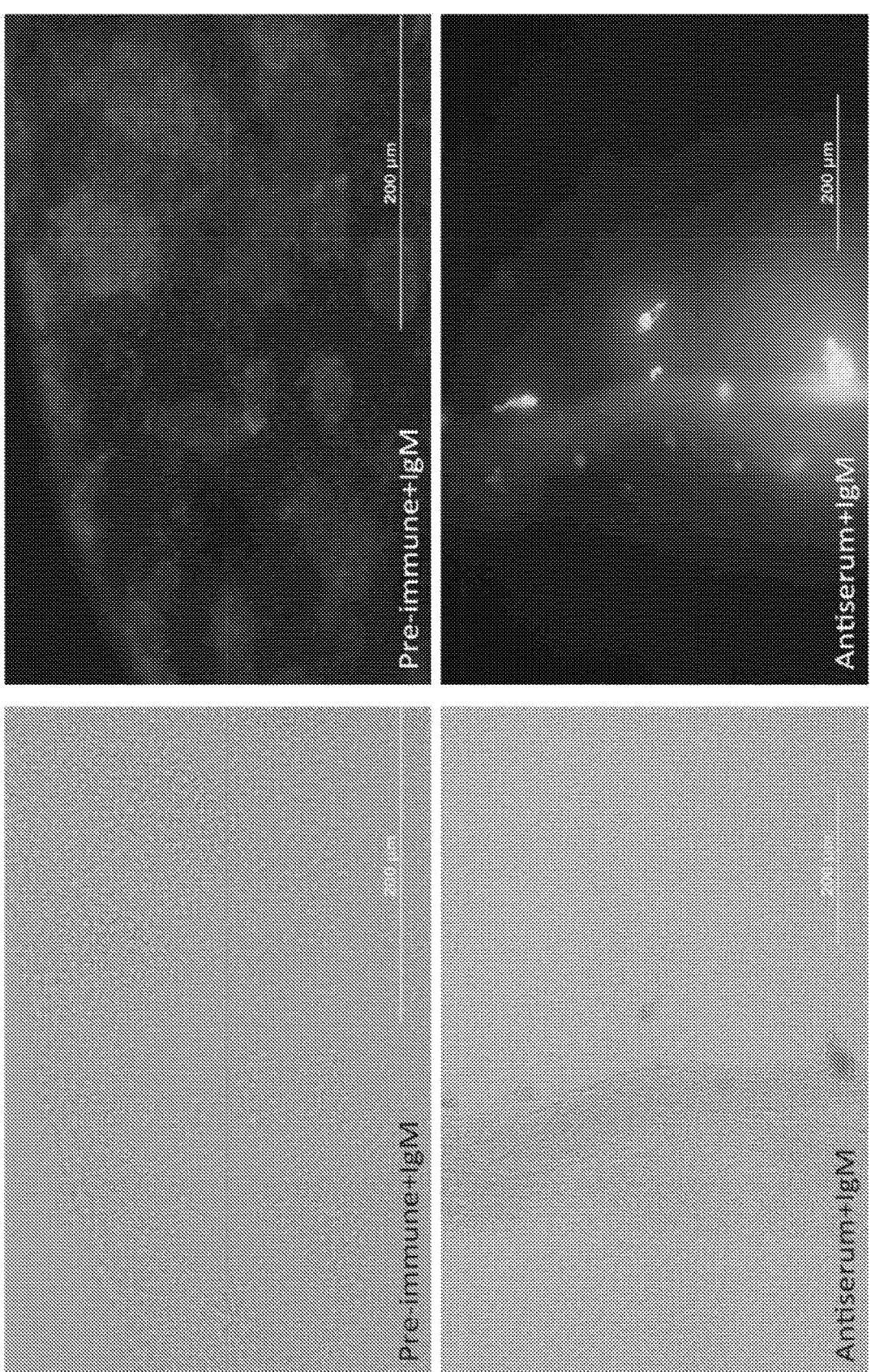

FIG. 6 shows that the addition of secondary antibodies (IgM) to biofilms pre-treated with antiserum undergo aggregation and clumping. Serum from rabbits before (pre-serum) or after immunization against Pf4 phage (anti-serum) was added to cultures of *P. aeruginosa* strain PA01. Then, a fluorescently labeled secondary antibody against rabbit IgM was used to visualize the clustering of bacteria. Confocal microscopy images are shown on the Left side of the image while fluorescence microscopy images are shown on the Right.

Figure 7:
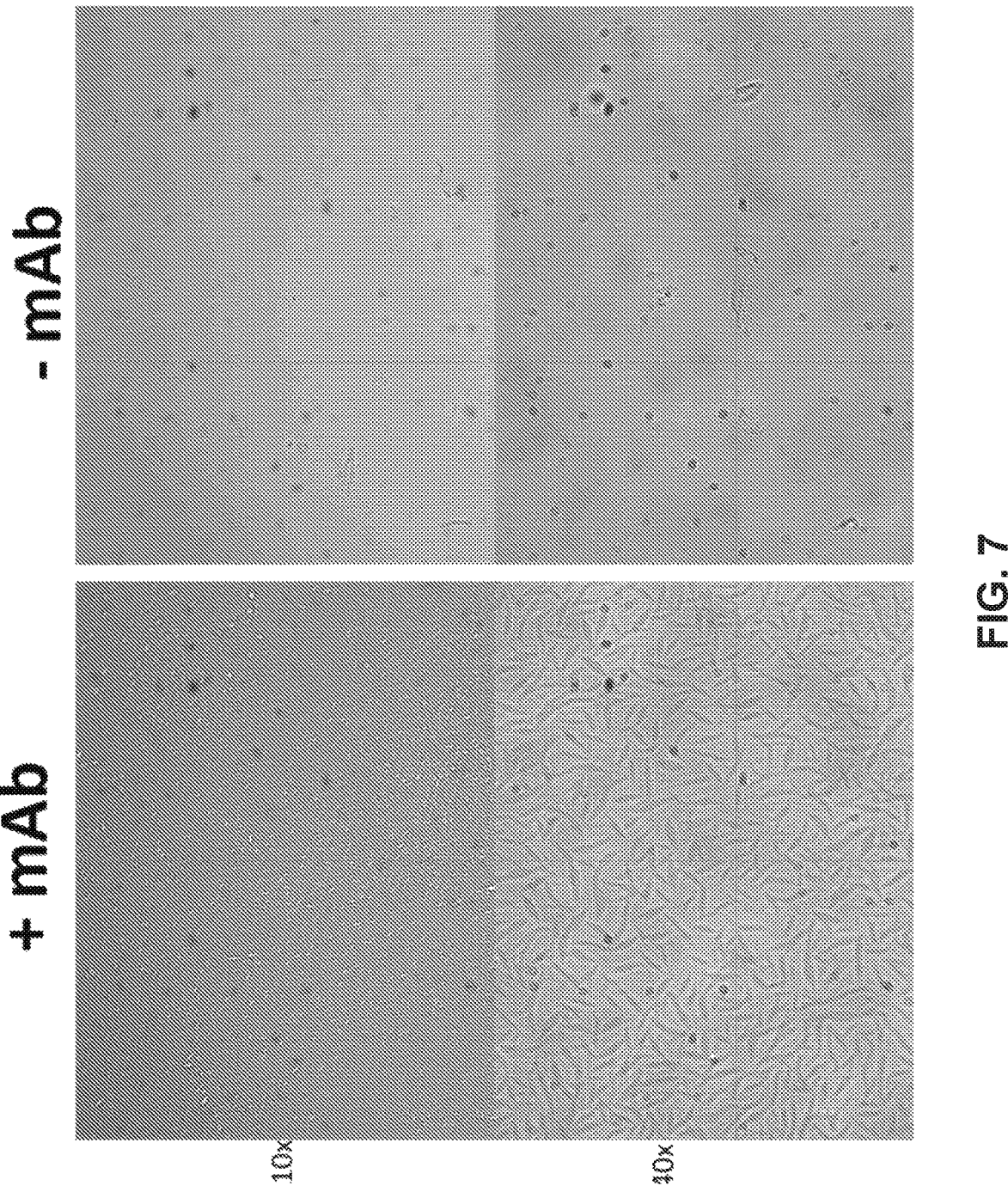

FIG. 7 shows that monoclonal antibody directed against Pf-family bacteriophage disrupt tactoidal (crystalline) structure formation by Pf4-polymer solutions. For these experiments, a panel of monoclonal antibodies were generated against the coat protein (CoaB) of Pf4 bacteriophage. All of these monoclonal antibodies had similar effects on tactoidal structures.

Figure 8:
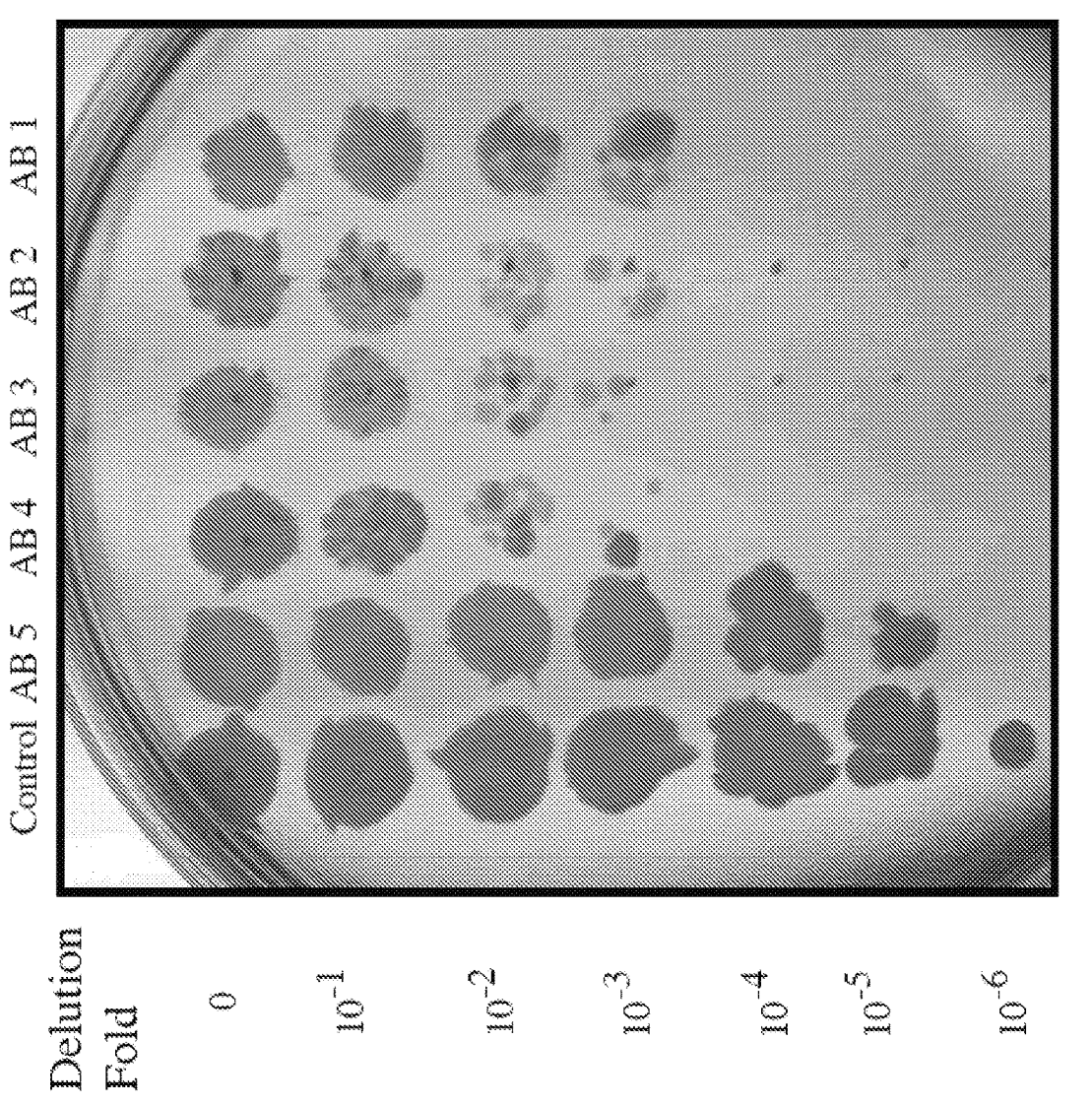

FIG. 8 shows a semi quantitative dot colony-forming assay that demonstrates that the anti-Pf4 monoclonal antibodies facilitate the penetration of antibiotics into biofilms (exposed to 10 µg/ml of Tobramycin). These experiments were performed by adding one of 4 monoclonal antibodies (AB1, AB2, AB3, AB4) that recognize Pf phage or a control antibody that does not recognize pf phage (AB5) to dilutions of biofilm cultures of the PA01 strain of *P. aeruginosa*. The size of the bacterial colonies that grow in this setting is inversely related to the penetration of antibiotic through the biofilm.

Figure 9:
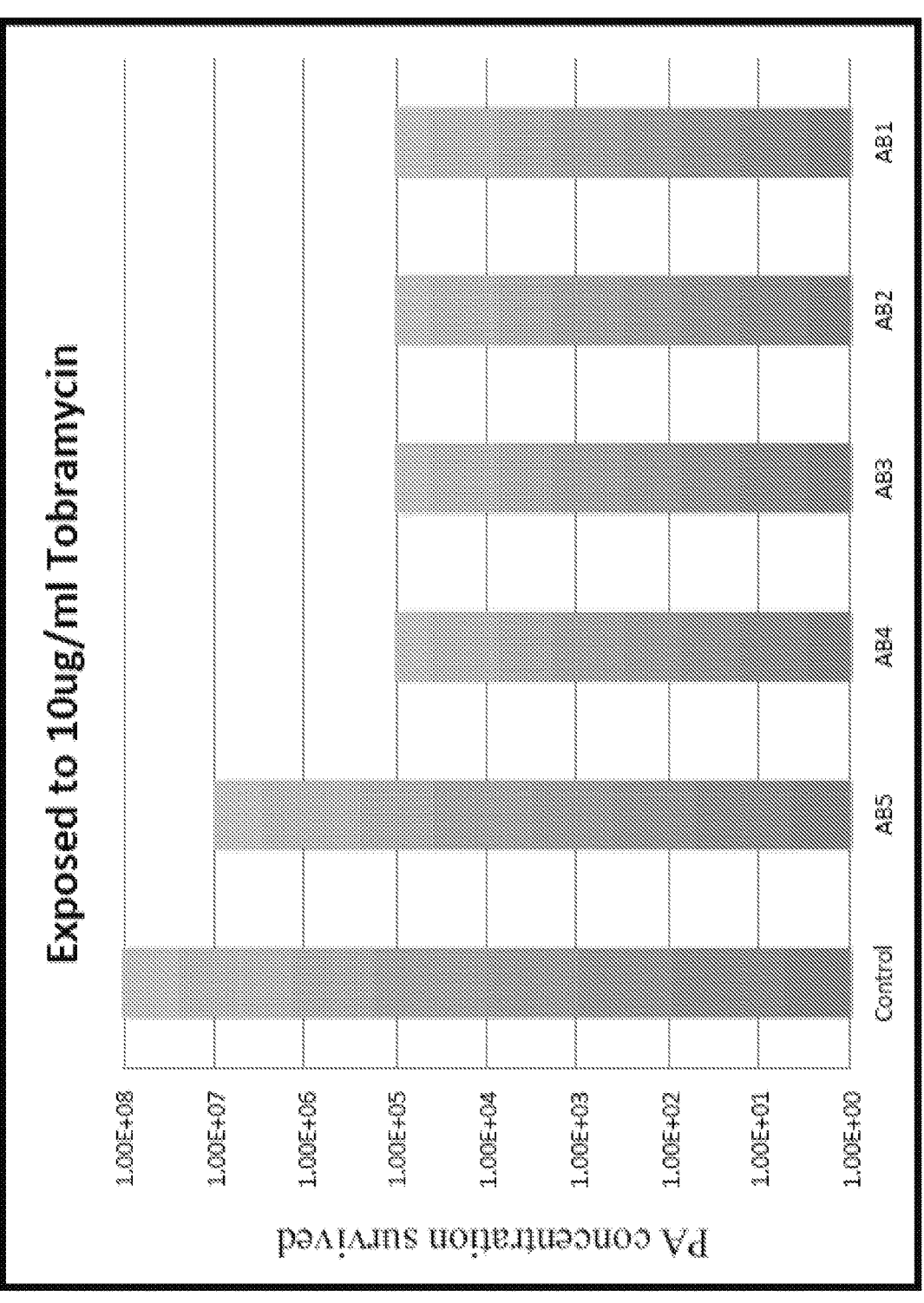

FIG. 9 shows PA concentration survived when exposed to anti-Pf4 antibodies and 10 µg/ml of Tobramycin. This figure provides quantification of the bacterial killing observed in FIG. 8.

Figure 10:
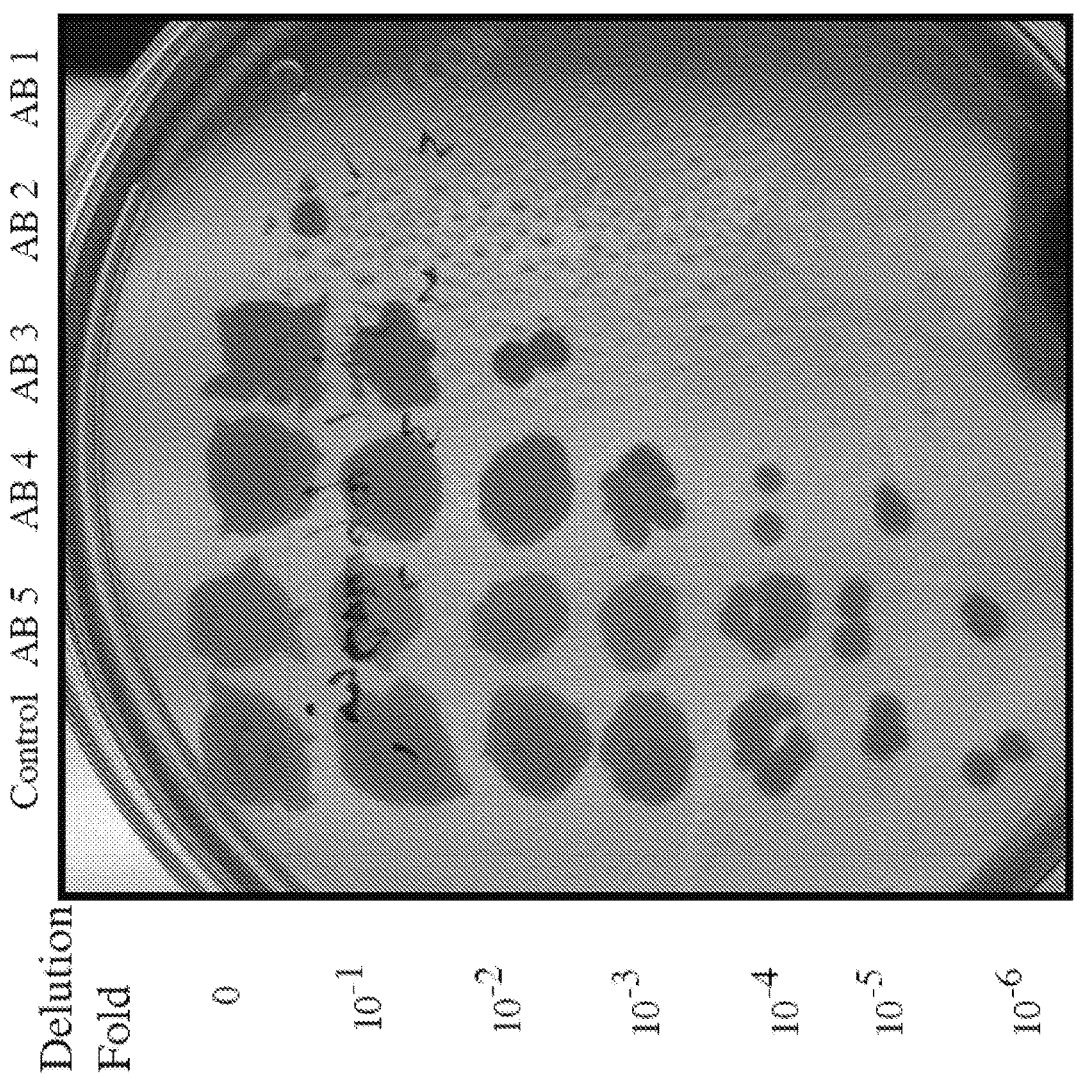

FIG. 10 shows a semi quantitative dot colony-forming assay that demonstrates that the anti-Pf4 antibodies facilitate the penetration of antibiotics into biofilms (exposed to 50 µg/ml of Tobramycin). These experiments were performed by adding one of 4 monoclonal antibodies (AB1, AB2, AB3, AB4) that recognize Pf phage or a control antibody that does not recognize pf phage (AB5) to dilutions of biofilm cultures of the PA01 strain of *P. aeruginosa*. The size of the bacterial colonies that grow in this setting is inversely related to the penetration of antibiotic through the biofilm. Compared to FIG. 8, these data show that the effect of the antibodies was more intense when the biofilms were exposed to higher concentration of Tobramycin (50 ug/ml compared to 10 µg/ml). In that case AB1 and AB2 cause to 7 orders of magnitude reduction in *P. aeruginosa* concentration that survived the Tobramycin treatment compared to the control.

Figure 11:
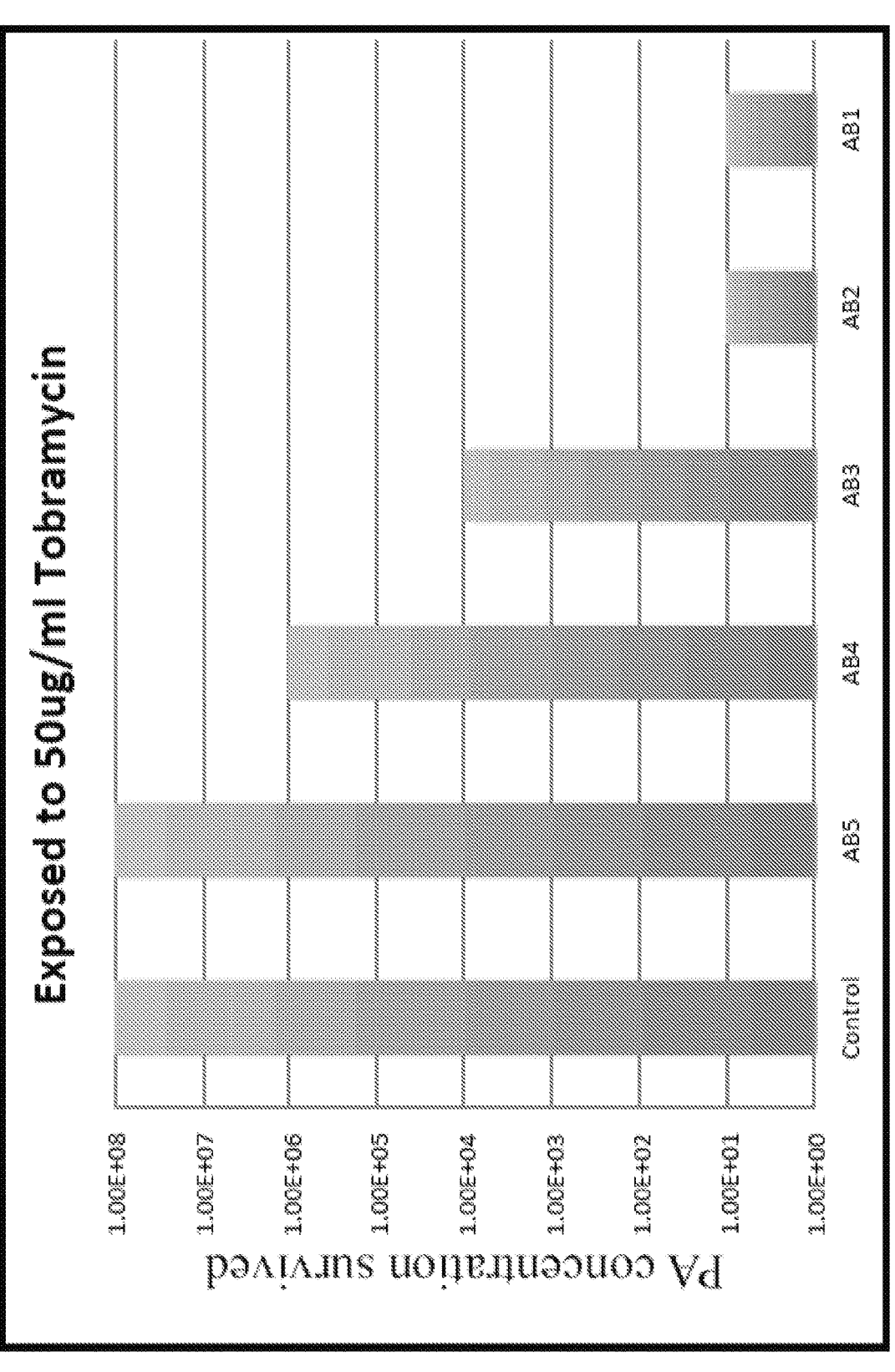
FIG. 11B: Representative images of rough and SCV colony biofilms showing transmitted light (displayed as l/lo) and birefringence (jsin(d)j).

FIG. 11 shows PA concentration survived when exposed to anti-Pf4 antibodies and 50 µg/ml of Tobramycin. This figure provides quantification of the bacterial killing observed in FIG. 10.

Figure 12:
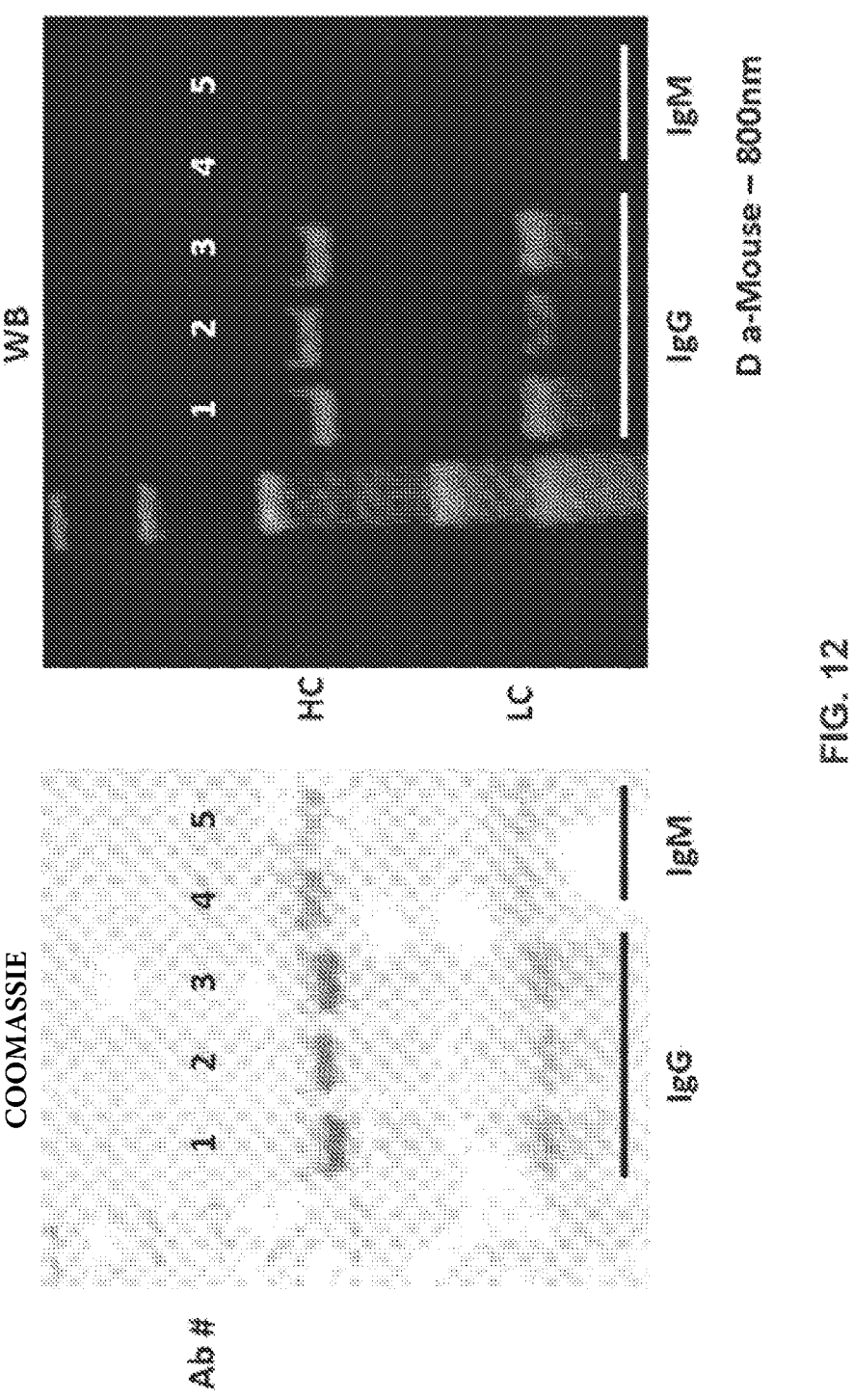

FIG. 12 shows detection of the heavy and light chains of 5 different monoclonal antibodies by COOMASSIE staining and by Western Blot (WB). Three of the antibodies are IgG and two of the antibodies are IgM. All of these antibodies were generated against the Pf phage coat protein sequence GVIDTSAVESAITDGQGDM (SEQ ID NO: 1).

Figure 13:
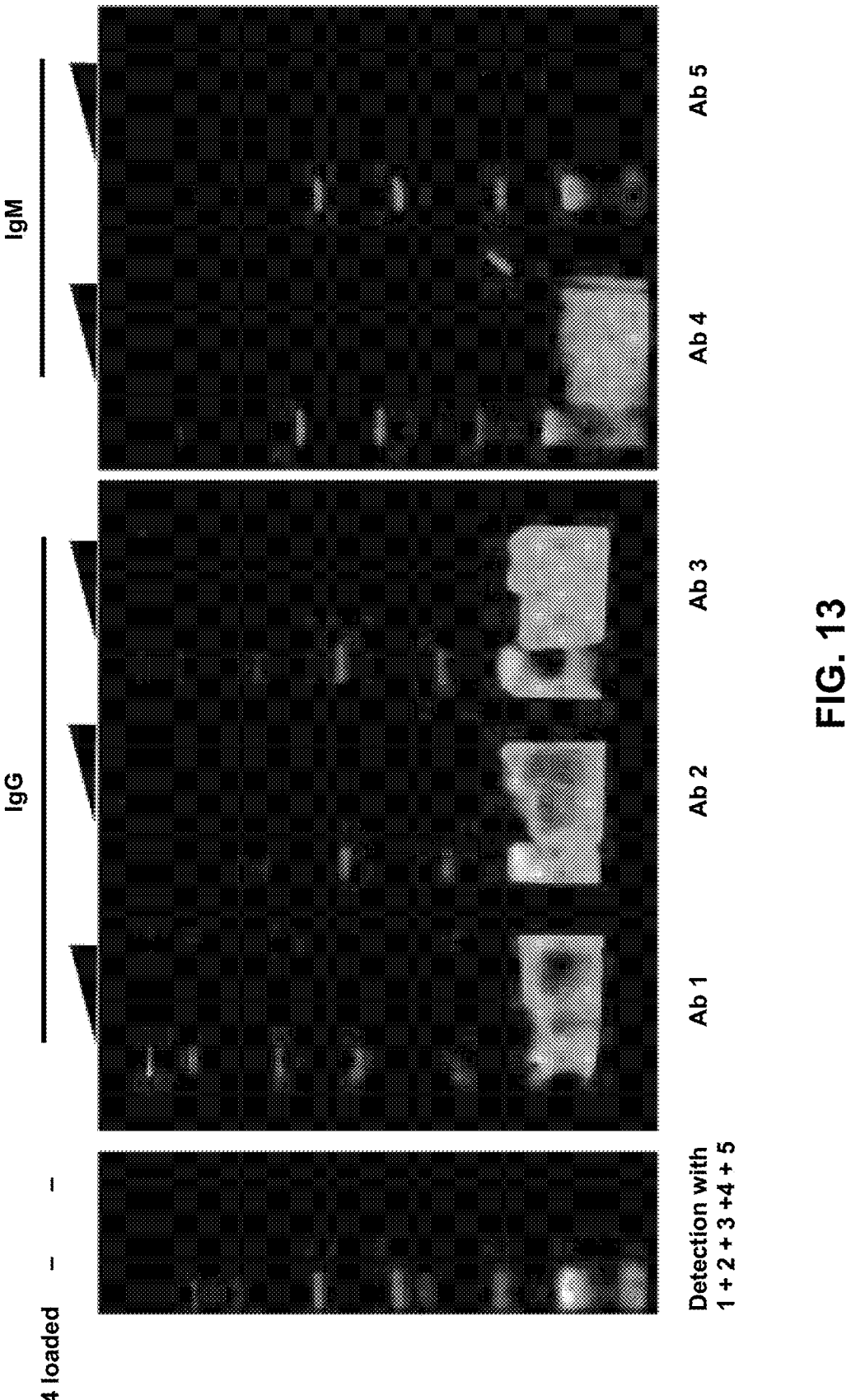

FIG. 13 shows detection of the CoaB coat protein of Pf bacteriophage by 5 different monoclonal antibodies by Western Blot (WB). Three of the antibodies are IgG and two of the antibodies are IgM. One of the IgM (Ab5) does not recognize Pf4 phage and is included here as a control.

DETAILED DESCRIPTION

Introduction

Pf-family bacteriophage play a heretofore unappreciated role in microbial biofilm formation. Monoclonal antibodies or immunizations directed against Pf-family bacteriophage provide protection against biofilm-associated infections with *P. aeruginosa* and other microbial pathogens. In particular, *P. aeruginosa* and other Gram-negative microbial pathogens can be resistant to multiple antibiotics, which is an enormous medical problem. Described herein are monoclonal antibodies and immunizations directed against Pf-family bacteriophage which can prevent biofilm formation by these microbes. Therefore, these monoclonal antibodies are an effective class of antibiotic.

In some embodiments, described herein are monoclonal antibodies (both IgG and IgM) directed against conserved regions on the CoaB coat protein of Pf-family bacteriophage. In other embodiments, described herein are synthetic peptides of these same conserved regions on the CoaB coat protein that can be used to immunize animals and human beings against Pf-family bacteriophage. Details of the methods and therapeutic agents of the present invention are provided in the following paragraphs.

Method for Treating/Preventing *P. aeruginosa* Infection

One aspect of the present invention relates to a method for treating or preventing *P. aeruginosa* infection in a human subject, which can be achieved by, for example, reducing or preventing *P. aeruginosa* biofilm formation. The method can comprise, for example, administering to the human subject a composition comprising (a) an antigen-binding polypeptide that binds Pf-family bacteriophage, or (b) a vaccine against Pf-family bacteriophage.

The human subject can be administered with, for example, one or more antigen-binding polypeptides as described herein. The antigen-binding polypeptide can be, for example, an antibody such as IgG or IgM. The antigen-binding polypeptide can bind specifically to, for example, a CoaB protein of Pf-family bacteriophage or fragment thereof. The CoaB protein or fragment thereof can be, for example, the CoaB protein of Pf4 bacteriophage. The CoaB protein or fragment thereof can comprise the amino acid sequence of, for example, GVIDTSAVESAITDGQGDM (SEQ ID NO:1).

The human subject can be administered with, for example, one or more antibiotics. The antibiotics can comprise a known antibiotic against *P. aeruginosa*, which includes but is not limited to, Aminoglycosides (including for example, tobramycin and gentamicin), Cephalosporins (including ceftazidime), and flouroquinolones (including ciprofloxacin). The antibiotics can be administered to the human subject either sequentially or simultaneously with the antigen-binding polypeptides. Without being bound by any theory, it is believed that the antigen-binding polypeptide could reduce or inhibit *P. aeruginosa* biofilm formation, thereby rendering the *P. aeruginosa* more susceptible to antibiotics.

The human subject can be, for example, infected with a *P. aeruginosa* strain resistant to one or more antibiotics. The human subject can be, for example, infected with one or more additional gram negative pathogens.

The human subject can be, for example, suffering from cystic fibrosis. The human subject can be, for example, suffering from burns. The human subject can be, for example, suffering from chronic wounds. The human subject can be, for example, suffering from chronic rhinosinusitis. The human subject can be, for example, suffering from ventilator-associated pneumonia. The human subject can be, for example, suffering from catheter-associated urinary tract infections. The human subject can be, for example, suffering from septic shock. The human subject can be, for example, suffering from gastrointestinal infections.

The human subject can be administered with, for example, a vaccine against Pf-family bacteriophage, such as Pf4 bacteriophage. The vaccine can comprise, for example, an immunogenic fragment of the CoaB protein of Pf-family bacteriophage as described herein.

The human subject being vaccinated can be, for example, an immune-compromised person, such as a person suffering from AIDS. The human subject being vaccinated can be, for example a person over 60 years old, or a person over 65 years old, or a person over 70 years old.

The vaccination can immunize the human subject against, for example, *P. aeruginosa* biofilm formation. The vaccination can immunize the human subject against, for example, *P. aeruginosa* infection.

Antibody Against Pf-Family Bacteriophage

Another aspect of the present invention relates to an antigen-binding polypeptide that binds specifically to CoaB protein of Pf-family bacteriophage or fragment thereof. The CoaB protein or fragment thereof can be, for example, the CoaB protein of Pf4 bacteriophage. The CoaB protein or fragment thereof can comprise the amino acid sequence of, for example, GVIDTSAVESAITDGQGDM (SEQ ID NO:1).

The antigen-binding polypeptide can be, for example, a monoclonal antibody, a chimeric antibody, a humanized antibody, a Fab fragment, a Fab' fragment, a F(ab')2 fragment, or an scFv molecule. The process for making antigen-binding polypeptides are described in, for example, WO/2008/094942, WO/2009/064854, and WO/2010/111180, which are incorporated by reference in their entireties. In one embodiment, the process comprises (a) immunizing a host with an immunogenic polypeptide of a Pf-family bacteriophage, such as an immunogenic fragment of the CoaB protein of Pf4 bacteriophage; and (b) harvesting the resulting antibody against the immunogenic polypeptide.

The antigen-binding polypeptide can be, for example, part of a fusion molecule. The fusion molecule can comprise, for example, a therapeutic or diagnostic agent conjugated to the antigen-binding polypeptide, as described in WO/2008/094942, WO/2009/064854, and WO/2010/111180.

The monoclonal antibodies can also be functionalized to better disrupt biofilms. The functionalized monoclonal antibodies can comprise, for example, enzymes that degrade constituents of the biofilm matrix, such as DNase I or alginate lyase, or charged molecules such as QDOTs or latex beads intended to alter the tertiary structure of the biofilm matrix. Functionalization can also consist of antibiotics, opsonins, reporter molecules, adjuvants, immunogens, or other proteins, carbohydrates or lipids conjugated to the antibodies.

In some embodiments, the antigen-binding polypeptide is an anti-Pf4 monoclonal antibody or fragment thereof. In some embodiments, the monoclonal antibody or fragment thereof specifically binds to the CoaB protein of Pf4 bacteriophage. In some embodiments, the monoclonal antibody or fragment thereof specifically binds to an antigenic fragment of the CoaB protein comprising, consisting essentially of or consisting of the amino acid sequence of GVIDTSAVE-SAITDGQGDM (SEQ ID NO:1). In some embodiments, the monoclonal antibody or fragment thereof has a humanized heavy chain variable region and a humanized light chain variable region.

In some embodiments, the anti-Pf4 monoclonal antibody or fragment thereof comprises a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8).

In some embodiments, the anti-Pf4 monoclonal antibody or fragment thereof comprises a heavy chain variable region comprising (1) the CDR-H1 comprising, consisting essentially of or consisting of the amino acid sequence of GYSFT-SYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18).

In some embodiments, the anti-Pf4 monoclonal antibody or fragment thereof comprises a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28).

In some embodiments, the anti-Pf4 monoclonal antibody or fragment thereof comprises a light chain variable region comprising (1) the CDR-L1 comprising, consisting essentially of or consisting of the amino acid sequence of QSLL-DSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the anti-Pf4 monoclonal antibody or fragment thereof comprises a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the anti-Pf4 monoclonal antibody or fragment thereof comprises a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the anti-Pf4 monoclonal antibody or fragment thereof comprises (a) a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8), and (b) a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the anti-Pf4 monoclonal antibody or fragment thereof comprises (a) a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18), and (b) a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the anti-Pf4 monoclonal antibody or fragment thereof comprises (a) a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28), and (b) a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the anti-Pf4 monoclonal antibody or fragment thereof comprises a heavy chain variable region comprising, consisting essentially of or consisting of the amino acid sequence of EVKLVESGGDLVKPGGSLKLS-CAASGFTFSSYVMSWVRQTPEKRLEWVASISSGG-STYYPDSVKGRFTIS RDNARNILYLQMSSLRSED-TAMYYCLRGQDYGAAYWGQGTLVTVSA (SEQ ID NO: 2) or a humanized version thereof.

In some embodiments, the anti-Pf4 monoclonal antibody or fragment thereof comprises a heavy chain variable region comprising, consisting essentially of or consisting of the amino acid sequence of EVQLQQSGTVLARP- GASVKMSCKASGYSFTSYWMHWVKQRPGQGLEWI-
GAIYPGNSDTSYNQKFKGKAKL TAVTSASTAYMEL-
SCLTNEDSAVFYCTRSQFYSGSSEDAMDYWGQGTS
VTVSS (SEQ ID NO: 12) or a humanized version thereof.

In some embodiments, the anti-Pf4 monoclonal antibody or fragment thereof comprises a heavy chain variable region comprising, consisting essentially of or consisting of the amino acid sequence of QIQLVQSGPELKKPGETVKIS-
CKASGYTFTNYGMNWLKQAPGKGLKWMGWIN-
TNTGEPTYAEEFKGRFAF SLETSASTAY-
LQINNLKNEDTATYFCARKDYRYWFAYWGQGTLVTV-
SA (SEQ ID NO: 22) or a humanized version thereof.

In some embodiments, the anti-Pf4 monoclonal antibody or fragment thereof comprises a light chain variable region comprising, consisting essentially of or consisting of the amino acid sequence of DVVMTQTPLTLSVTIGQPASIS-
CKSSQSLLDSDGKTYLNWLLQRPGQSPKRLIYLVSK-
LDSGVPDRFTGS GSGTDFTLKISRVEAE-
DLGVYYCWQGTHFPQTFGGGTKLEIK (SEQ ID NO: 4) or a humanized version thereof.

In some embodiments, the anti-Pf4 monoclonal antibody or fragment thereof comprises a light chain variable region comprising, consisting essentially of or consisting of the amino acid sequence of DVLMTQTPLSLPVSLGDQASIS-
CRSSQSIVHSNGN-
TYLEWYLQKPGQSPKLLIYKVSNRFSGVPDRFSGS
GSGTDFTLKISRVEAE-
DLGVYFCFQGSHVPWTFGGGTKLEIK (SEQ ID NO: 14) or a humanized version thereof.

In some embodiments, the anti-Pf4 monoclonal antibody or fragment thereof comprises a light chain variable region comprising, consisting essentially of or consisting of the amino acid sequence of DVLMTQTPLSLPVSLGDQASIS-
CRSSQSIVHSNGN-
TYLEWYLQKPGQSPKLLIYKVSNRFSGVPDRFSGS
GSGTDFTLKISRVEAE-
DLGVYYCFQGSHVPFTFGSGTKLEIK (SEQ ID NO: 24) or a humanized version thereof.

Another aspect of the present invention relates to a pharmaceutical composition comprising (a) the antigen-binding polypeptide described herein or a fusion molecule comprising the antigen-binding polypeptide, and (b) a pharmaceutically acceptable carrier. In one embodiment, the active ingredient of the pharmaceutical composition consists essentially of the antigen-binding polypeptide or fusion molecule. In another embodiment, the active ingredient of the pharmaceutical composition consists of the antigen-binding polypeptide or fusion molecule.

Another aspect of the present invention relates to a polynucleotide encoding the antigen-binding polypeptide described herein. The polynucleotide encoding the antigen-binding polypeptide can be comprised in, for example, an expression cassette, with optionally a promoter operably linked to the polynucleotide. The expression cassette can be comprised in, for example, a plasmid or transformation vector. The plasmid or transformation vector can be used to obtain a transformed cell capable of producing the antigen-binding polypeptide encoded therein.

In some embodiments, the polynucleotide encodes a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8).

In some embodiments, the polynucleotide encodes a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18).

In some embodiments, the polynucleotide encodes a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28).

In some embodiments, the polynucleotide encodes a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the polynucleotide encodes a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the polynucleotide encodes a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the polynucleotide encodes (a) a heavy chain variable region comprising (1) the CDR-H1 comprising, consisting essentially of or consisting of the amino acid sequence of GFTFSSYV (SEQ ID NO: 6); (2) the CDR-H2 comprising, consisting essentially of or consisting of the amino acid sequence of ISSGGST (SEQ ID NO: 7); and (3) the CDR-H3 comprising, consisting essentially of or consisting of the amino acid sequence of LRGQDYGAAY (SEQ ID NO: 8), and (b) a light chain variable region comprising (1) the CDR-L1 comprising, consisting essentially of or consisting of the amino acid sequence of QSLLDSDGKTY (SEQ ID NO: 9); (2) the CDR-L2 comprising, consisting essentially of or consisting of the amino acid sequence of LVS (SEQ ID NO: 10); and (3) the CDR-L3 comprising, consisting essentially of or consisting of the amino acid sequence of WQGTHFPQT (SEQ ID NO: 11).

In some embodiments, the polynucleotide encodes (a) a heavy chain variable region comprising (1) the CDR-H1 comprising, consisting essentially of or consisting of the amino acid sequence of GYSFTSYW (SEQ ID NO: 16); (2) the CDR-H2 comprising, consisting essentially of or consisting of the amino acid sequence of IYPGNSDT (SEQ ID NO: 17); and (3) the CDR-H3 comprising, consisting essentially of or consisting of the amino acid sequence of TRSQFYSGSSEDAMDY (SEQ ID NO: 18), and (b) a light chain variable region comprising (1) the CDR-L1 comprising, consisting essentially of or consisting of the amino acid sequence of QSIVHSNGNTY (SEQ ID NO: 19); (2) the CDR-L2 comprising, consisting essentially of or consisting of the amino acid sequence of KVS (SEQ ID NO: 20); and (3) the CDR-L3 comprising, consisting essentially of or consisting of the amino acid sequence of FQGSHVPWT (SEQ ID NO: 21).

In some embodiments, the polynucleotide encodes (a) a heavy chain variable region comprising (1) the CDR-H1 comprising, consisting essentially of or consisting of the amino acid sequence of GYTFTNYG (SEQ ID NO: 26); (2) the CDR-H2 comprising, consisting essentially of or consisting of the amino acid sequence of INTNTGEP (SEQ ID NO: 27); and (3) the CDR-H3 comprising, consisting essentially of or consisting of the amino acid sequence of ARKDYRYWFAY (SEQ ID NO: 28), and (b) a light chain variable region comprising (1) the CDR-L1 comprising, consisting essentially of or consisting of the amino acid sequence of QSIVHSNGNTY (SEQ ID NO: 29); (2) the CDR-L2 comprising, consisting essentially of or consisting of the amino acid sequence of KVS (SEQ ID NO: 30); and (3) the CDR-L3 comprising, consisting essentially of or consisting of the amino acid sequence of FQGSHVPFT (SEQ ID NO: 31).

In some embodiments, the polynucleotide encodes a heavy chain variable region comprising, consisting essentially of or consisting of the amino acid sequence of EVKLVESGGDLVKPGGSLKLS-CAASGFTFSSYVMSWVRQTPEKRLEWVASISSGG-STYYPDSVKGRFTIS RDNARNILYLQMSSLRSED-TAMYYCLRGQDYGAAYWGQGTLVTVSA (SEQ ID NO: 2) or a humanized version thereof.

In some embodiments, the polynucleotide encodes a heavy chain variable region comprising, consisting essentially of or consisting of the amino acid sequence of EVQLQQSGTVLARPGASVKMSCKASGYSFT-SYWMHWVKQRPGQGLEWIGAIYPGNSDTSYN-QKFKGKAKL TAVTSASTAYMELSCLTNEDSAVFYC-TRSQFYSGSSEDAMDYWGQGTSVTVSS (SEQ ID NO: 12) or a humanized version thereof.

In some embodiments, the polynucleotide encodes a heavy chain variable region comprising, consisting essentially of or consisting of the amino acid sequence of QIQLVQSGPELKKPGETVKISCK-ASGYTFTNYGMNWLKQAPGKGLKWMGWINTNT-GEPTYAEEFKGRFAF SLETSASTAYLQINNLKNED-TATYFCARKDYRYWFAYWGQGTLVTVSA (SEQ ID NO: 22) or a humanized version thereof.

In some embodiments, the polynucleotide encodes a light chain variable region comprising, consisting essentially of or consisting of the amino acid sequence of DVVMTQTPLTLSVTIGQPASISCKSSQSLL-DSDGKTYLNWLLQRPGQSPKRLIYLVSK-LDSGVPDRFTGS GSGTDFTLKISRVEAE-DLGVYYCWQGTHFPQTFGGGTKLEIK (SEQ ID NO: 4) ora humanized version thereof.

In some embodiments, the polynucleotide encodes a light chain variable region comprising, consisting essentially of or consisting of the amino acid sequence of DVLMTQTPLSLPVSLGDQASISCRSSQSIVHSNGN-TYLEWYLQKPGQSPKLLIYKVSNRFSGVPDRFSGS GSGTDFTLKISRVEAE- DLGVYFCFQGSHVPWTFGGGTKLEIK (SEQ ID NO: 14) or a humanized version thereof.

In some embodiments, the polynucleotide encodes a light chain variable region comprising, consisting essentially of or consisting of the amino acid sequence of DVLMTQTPLSLPVSLGDQASISCRSSQSIVHSNGN-TYLEWYLQKPGQSPKLLIYKVSNRFSGVPDRFSGS GSGTDFTLKISRVEAE-DLGVYYCFQGSHVPFTFGSGTKLEIK (SEQ ID NO: 24) or a humanized version thereof.

Vaccine Against Pf-Family Bacteriophage

A further aspect of the present invention relates to a vaccine against Pf-family bacteriophage, comprising an immunogenic fragment of the CoaB protein of Pf-family bacteriophage. The CoaB protein or fragment thereof can be, for example, the CoaB protein of Pf4 bacteriophage. The CoaB protein or fragment thereof can comprise the amino acid sequence of, for example, GVIDTSAVE-SAITDGQGDM (SEQ ID NO:1).

In some embodiments, the vaccine is used to vaccinate patients newly diagnosed with cystic fibrosis before they become colonized with *P. aeruginosa* or to elderly people before they become prone to catheter infections and hospital-acquired infections. In some embodiments, the vaccine is used to vaccinate nursing home populations, or patients undergoing dialysis, mechanical ventilation or recurrent UTIs, or burn victims.

These and other features, together with the organization and manner of operation thereof, will become apparent from the following detailed description when taken in conjunction with the accompanying drawings.

Working Examples

It has been recently reported that a bacteriophage/virus produced by the bacteria *Pseudomonas aeruginosa* contributes to the formation and function of *Pseudomonas aeruginosa* biofilms. In particular, it has been reported that Pf bacteriophage assemble biofilms into a liquid crystal and that this crystalline organization contributes to biofilm function, including adhesiveness and antibiotic tolerance. See Secor et al., Cell Host & Microbe., 18(5):549-559 (2015). In light of these data implicating Pf bacteriophages in biofilm structure and function, vaccines and monoclonal antibodies that target Pf bacteriophages have been generated to disrupt *Pseudomonas aeruginosa* biofilms.

Example 1—Role of Pf-Family Phage in Biofilm Formation

Filamentous bacteriophage are produced by *P. aeruginosa* during the biofilm mode of growth (see Rice et al., The ISME Journal (2009) 3, 271-282). A mutant not capable of producing Pf4, PA0728 (FIGS. 2A and 2B) (see Castang and Dove, *J Bacteriol*. September 2012; 194(18): 5101-5109), exhibited differences in morphology (FIG. 2C), adhesion (FIG. 2D), antibiotic susceptibility (FIG. 2E), and matrix organization (birefringence, FIG. 2F).

Example 2—Inhibition of Biofilms by Antiserum

The method of preventing biofilm formation by creating vaccines and monoclonal antibodies that target Pf bacteriophage was evaluated. Specifically, rabbits were immunized with CoaB peptide, and the ability of their sera to neutralize biofilm formation was examined. This antiserum was found to inhibit biofilm formation, alter antibiotic tolerance (FIG.

Figures 1A, 1B, 1C, 1D:
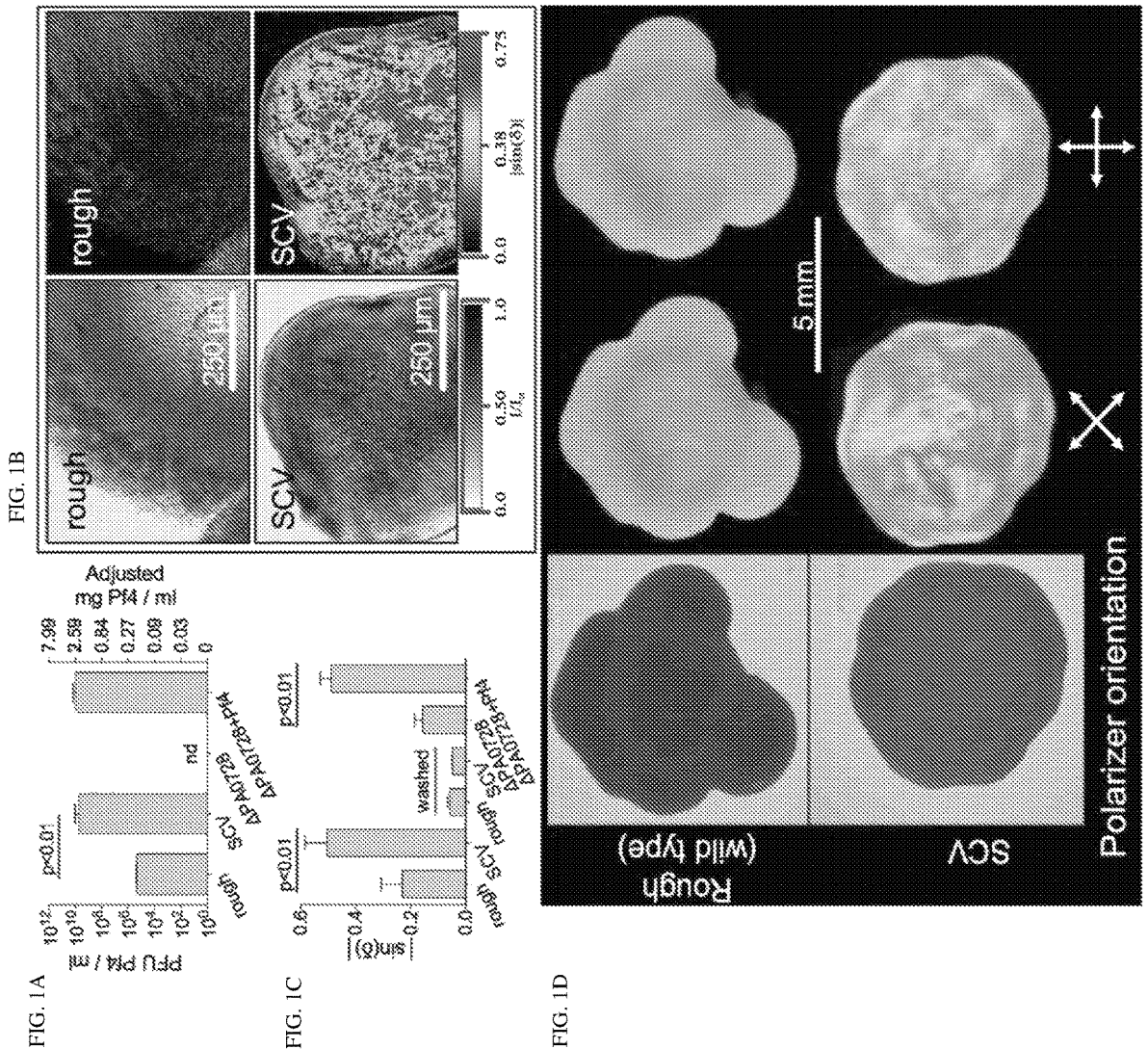
FIG. 1A-1D. Pf 4 bacteriophage organizes *P. aeruginosa* biofilms into a liquid crystalline structure.
Figure 3:
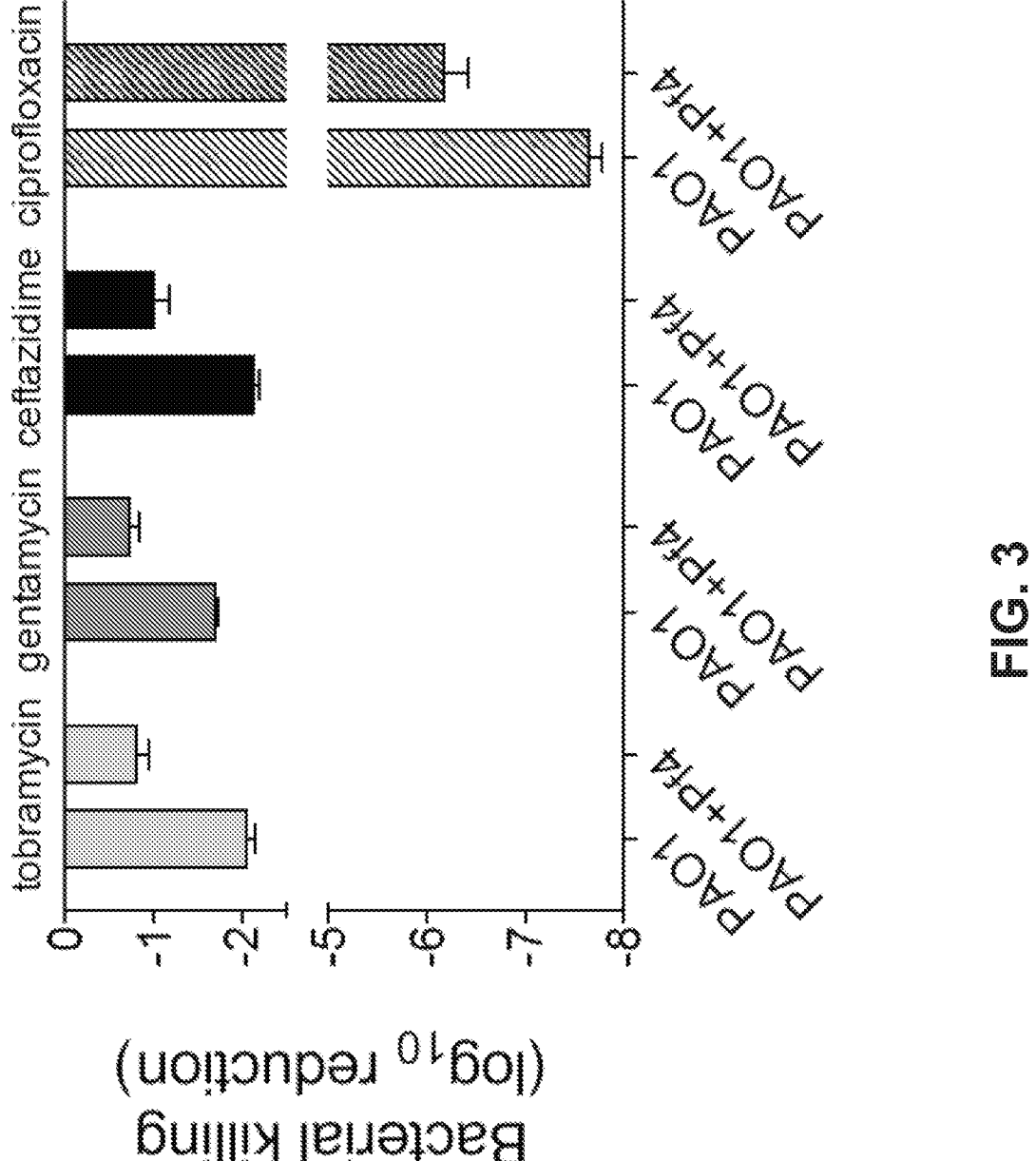
FIG. 3 shows that supplementation of *P. aeruginosa* strain PA01 with Pf4 bacteriophage makes these colonies more tolerant to multiple antibiotics. Killing is represented as the log 10 reduction of viable cells recovered from cultures treated with different antibiotics, all at 10 mg/ml, compared to untreated controls. Results are mean±SD of three experiments.
Figure 4:
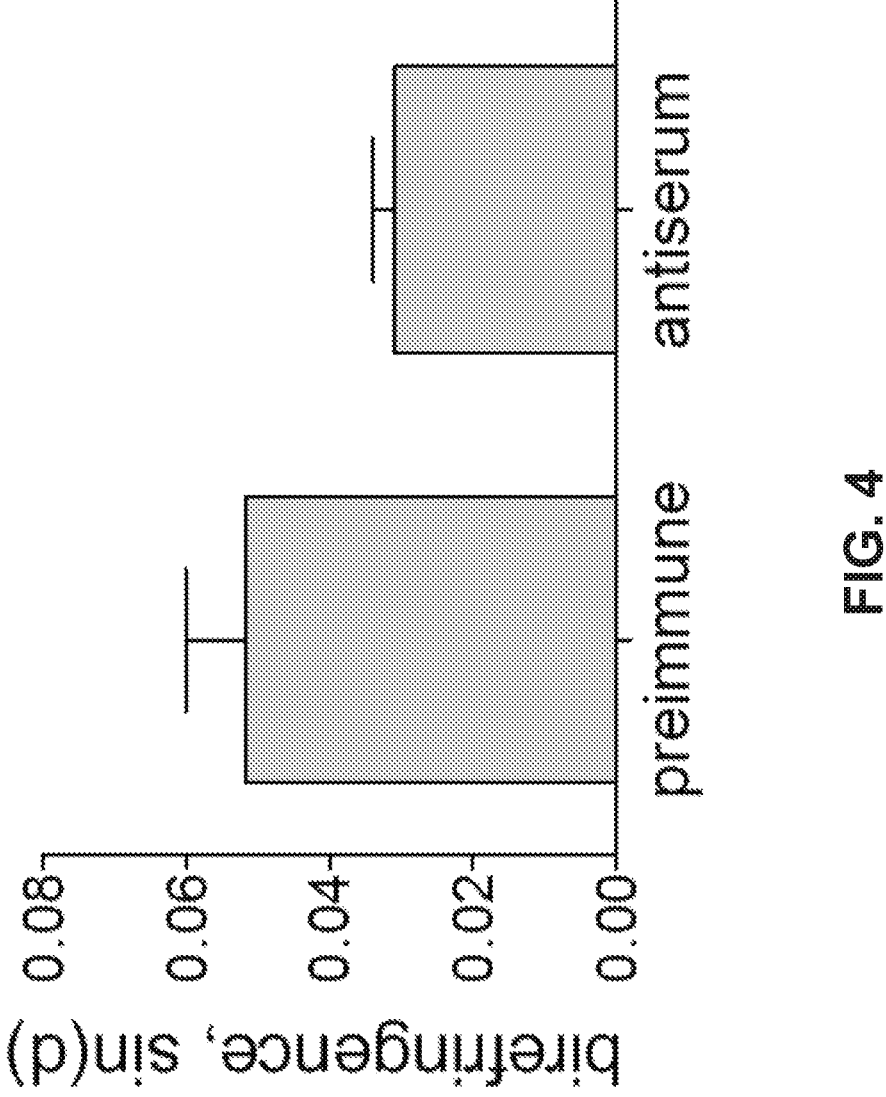
FIG. 4 shows that serum from rabbits immunized with whole Pf phage prevents biofilm formation. Biofilm formation was assayed by quantification of birefringence (liquid crystal-like organization of the biofilm matrix) of PA01 cultures 18 h after seeding and treatment with serum from rabbits before or after immunization against Pf4 phage.

3), and alter the overall organization of the biofilm matrix (reduced birefringence, FIG. 4), suggesting that anti-CoaB antibodies present in the serum are capable of disrupting *P. aeruginosa* biofilms producing the filamentous bacteriophage Pf4. The addition of secondary antibodies (e.g., fluorescently labeled anti-rabbit IgG and IgM) to *P. aeruginosa* biofilms pre-treated with anti-Pf4 antibodies altered the gross morphology of *P. aeruginosa* biofilms (FIGS. 5 and 6).

Example 3—Production of Monoclonal Antibody

Monoclonal antibodies that target Pf4, including three IgG and two IgM antibodies, were developed as a new class of anti-microbial for use against multi-drug resistant *P. aeruginosa*. These antibodies were generated using standard, well-established techniques, generally as described in hypertext transfer protocol www.currentprotocols.com/WileyCDA/CPUnit/refld-im0205.html. In brief, the CoaB peptide in question was conjugated to immunogenic proteins in order to elicit an immune response in rabbits and/or mice. Clones were then isolated from individual animals with strong serum responses to the peptide in question and these were fused to competent cells to generate hybridomas. These were then grown in culture and monoclonal antibodies were harvested from the cell culture supernatants. The specificity of these against CoaB peptide was then confirmed and five clones with the greatest specificity were selected for further development.

The variable regions of the three mouse IgG anti-Pf4 monoclonal antibodies were sequenced. The VH, VL, and CDR sequences of IgG Ab #1 (1A8), IgG Ab #2 (2D4) and IgG Ab #3 (3D6) are provided below.

```
IgG Ab #1 VH:
                                   (SEQ ID NO: 2)
EVKLVESGGDLVKPGGSLKLSCAASGFTFSSYVMSWVRQTPEKRLEWVAS

ISSGGSTYYPDSVKGRFTISRDNARNILYLQMSSLRSEDTAMYYCLRGQD

YGAAYWGQGTLVTVSA.
                                   (SEQ ID NO: 3)
GAAGTGAAGCTGGTGGAGTCTGGGGGAGACTTAGTGAAGCCTGGAGGGTC

CCTGAAACTCTCCTGTGCAGCCTCTGGATTCACTTTCAGTAGCTATGTCA

TGTCTTGGGTTCGCCAGACTCCAGAAAAGAGGCTGGAGTGGGTCGCATCC

ATTAGTAGTGGTGGTAGCACCTACTATCCAGACAGTGTGAAGGGCCGATT

CACCATCTCCAGAGATAATGCCAGGAACATCCTGTACCTGCAAATGAGTA

GTCTGAGGTCTGAGGACACGGCCATGTATTACTGTTTAAGAGGCCAGGAC

TACGGCGCCGCTTACTGGGGCCAAGGGACTCTGGTCACTGTCTCTGCA.

IgG Ab #1 VL:
                                   (SEQ ID NO: 4)
DVVMTQTPLTLSVTIGQPASISCKSSQSLLDSDGKTYLNWLLQRPGQSPK

RLIYLVSKLDSGVPDRFTGSGSGTDFTLKISRVEAEDLGVYYCWQGTHFP

QTFGGGTKLEIK.
                                   (SEQ ID NO: 5)
GATGTTGTGATGACCCAGACTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT
```

```
CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CAGACGTTCGGTGGAGGCACCAAGCTGGAAATCAAA.

IgG Ab #1 CDR:
CDR-H1 -
                                   (SEQ ID NO: 6)
GFTFSSYV.
CDR-H2 -
                                   (SEQ ID NO: 7)
ISSGGST.
CDR-H3 -
                                   (SEQ ID NO: 8)
LRGQDYGAAY.
CDR-L1 -
                                   (SEQ ID NO: 9)
QSLLDSDGKTY.
CDR-L2 -
                                   (SEQ ID NO: 10)
LVS.
CDR-L3 -
                                   (SEQ ID NO: 11)
WQGTHFPQT.

IgG Ab #2 VH:
                                   (SEQ ID NO: 12)
EVQLQQSGTVLARPGASVKMSCKASGYSFTSYWMHWVKQRPGQGLEWIGA

IYPGNSDTSYNQKFKGKAKLTAVTSASTAYMELSCLTNEDSAVFYCTRSQ

FYSGSSEDAMDYWGQGTSVTVSS.
                                   (SEQ ID NO: 13)
GAGGTTCAGCTCCAGCAGTCTGGGACTGTGCTGGCAAGGCCTGGGGCTTC

CGTGAAGATGTCCTGCAAGGCTTCTGGCTACAGCTTTACCAGCTACTGGA

TGCACTGGGTAAAACAGAGGCCTGGACAGGGTCTAGAATGGATTGGTGCT

ATTTATCCTGGAAATAGTGATACTAGTTACAACCAGAAGTTCAAGGGCAA

GGCCAAACTGACTGCAGTCACATCCGCCAGCACTGCCTACATGGAGCTCA

GCTGCCTGACAAATGAGGACTCTGCGGTCTTTTACTGTACAAGATCCCAA

TTTTACTCCGGTAGTAGCGAGGATGCTATGGACTACTGGGGTCAAGGAAC

CTCAGTCACCGTCTCCTCA.

IgG Ab #2 VL:
                                   (SEQ ID NO: 14)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYFCFQGSHVP

WTFGGGTKLEIK.
                                   (SEQ ID NO: 15)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTTCTGCTTTCAAGGTTCACATGTTCCG

TGGACGTTCGGTGGAGGCACCAAGCTGGAAATCAAA.

IgG Ab #2 CDR:
CDR-H1 -
```

-continued (SEQ ID NO: 16)
GYSFTSYW.

CDR-H2 -
(SEQ ID NO: 17)
IYPGNSDT.

CDR-H3 -
(SEQ ID NO: 18)
TRSQFYSGSSEDAMDY.

CDR-L1 -
(SEQ ID NO: 19)
QSIVHSNGNTY.

CDR-L2 -
(SEQ ID NO: 20)
KVS.

CDR-L3 -
(SEQ ID NO: 21)
FQGSHVPWT.

IgG Ab #3 VH:
(SEQ ID NO: 22)
QIQLVQSGPELKKPGETVKISCKASGYTFTNYGMNWLKQAPGKGLKWMGW

INTNTGEPTYAEEFKGRFAFSLETSASTAYLQINNLKNEDTATYFCARKD

YRYWFAYWGQGTLVTVSA.

(SEQ ID NO: 23)
CAGATCCAGTTGGTGCAGTCTGGACCTGAGCTGAAGAAGCCTGGAGAGAC

AGTCAAGATCTCCTGCAAGGCTTCTGGGTATACCTTCACAAACTATGGAA

TGAACTGGCTGAAGCAGGCTCCAGGAAAGGGTTTAAAGTGGATGGGCTGG

ATAAACACCAACACTGGAGAGCCAACATATGCTGAAGAGTTCAAGGGACG

GTTTGCCTTCTCTTTGGAAACCTCTGCCAGCACTGCCTATTTGCAGATCA

ACAACCTCAAAAATGAGGACACGGCTACATATTTCTGTGCAAGAAAGGAC

TATAGGTACTGGTTTGCTTACTGGGGCCAAGGGACTCTGGTCACTGTCTC

TGCA.

IgG Ab #3 VL:
(SEQ ID NO: 24)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

FTFGSGTKLEIK.

(SEQ ID NO: 25)
GATGTTTTGATGACCCAAACTCCACTCTCCCTGCCTGTCAGTCTTGGAGA

TCAAGCCTCCATCTCTTGCAGATCTAGTCAGAGCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCA

TTCACGTTCGGCTCGGGGACAAAGTTGGAAATAAAA.

IgG Ab #3 CDR:
CDR-H1 -
(SEQ ID NO: 26)
GYTFTNYG.

CDR-H2 -
(SEQ ID NO: 27)
INTNTGEP.

CDR-H3 -

-continued (SEQ ID NO: 28)
ARKDYRYWFAY.

CDR-L1 -
(SEQ ID NO: 29)
QSIVHSNGNTY.

CDR-L2 -
(SEQ ID NO: 30)
KVS.

CDR-L3 -
(SEQ ID NO: 31)
FQGSHVPFT.

Example 4—Inhibition of Biofilms by Monoclonal Antibody

Also tested is whether the monoclonal antibodies produced according to Example 2 can serve as effective antibiotic drugs that could be used in conjunction with conventional antibiotics, as current therapeutic options for treatment of multidrug-resistant *P. aeruginosa* are very limited. As shown in FIG. 7, the mAbs prevented liquid crystal formation of Pf4-polymer solutions suggesting that the mAbs have the same activities as the anti-Pf4 antibodies present in the antiserum of Example 2.

As used herein, the singular terms "a," "an," and "the" include plural referents unless the context clearly dictates otherwise. Thus, for example, reference to a marker can include multiple markers unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations, which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/ or variation of the concepts herein disclosed may be resorted to by those skilled in the art, and that such modifications and variations are considered to be within the scopes of this invention.

```
                          SEQUENCE LISTING

Sequence total quantity: 31
SEQ ID NO: 1              moltype = AA  length = 19
FEATURE                   Location/Qualifiers
source                    1..19
                          mol_type = protein
                          organism = Pseudomonas aeruginosa
SEQUENCE: 1
GVIDTSAVES AITDGQGDM                                                 19

SEQ ID NO: 2              moltype = AA  length = 116
FEATURE                   Location/Qualifiers
source                    1..116
                          mol_type = protein
                          organism = Mus musculus
SEQUENCE: 2
EVKLVESGGD LVKPGGSLKL SCAASGFTFS SYVMSWVRQT PEKRLEWVAS ISSGGSTYYP   60
DSVKGRFTIS RDNARNILYL QMSSLRSEDT AMYYCLRGQD YGAAYWGQGT LVTVSA       116

SEQ ID NO: 3              moltype = AA  length = 348
FEATURE                   Location/Qualifiers
source                    1..348
                          mol_type = protein
                          organism = Mus musculus
SEQUENCE: 3
GAAGTGAAGC TGGTGGAGTC TGGGGGAGAC TTAGTGAAGC CTGGAGGGTC CCTGAAACTC   60
TCCTGTGCAG CCTCTGGATT CACTTTCAGT AGCTATGTCA TGTCTTGGGT TCGCCAGACT  120
CCAGAAAAGA GGCTGGAGTG GGTCGCATCC ATTAGTAGTG GTGGTAGCAC CTACTATCCA  180
GACAGTGTGA AGGGCCGATT CACCATCTCC AGAGATAATG CCAGGAACAT CCTGTACCTG  240
CAAATGAGTA GTCTGAGGTC TGAGGACACG GCCATGTATT ACTGTTTAAG AGGCCAGGAC  300
TACGGCGCCG CTTACTGGGG CCAAGGGACT CTGGTCACTG TCTCTGCA               348

SEQ ID NO: 4              moltype = AA  length = 112
FEATURE                   Location/Qualifiers
source                    1..112
                          mol_type = protein
                          organism = Mus musculus
SEQUENCE: 4
DVVMTQTPLT LSVTIGQPAS ISCKSSQSLL DSDGKTYLNW LLQRPGQSPK RLIYLVSKLD   60
SGVPDRFTGS GSGTDFTLKI SRVEAEDLGV YYCWQGTHFP QTFGGGTKLE IK          112

SEQ ID NO: 5              moltype = DNA  length = 336
FEATURE                   Location/Qualifiers
source                    1..336
                          mol_type = other DNA
                          organism = Mus musculus
SEQUENCE: 5
gatgttgtga tgacccagac tccactcact ttgtcggtta ccattggaca accagcctcc   60
atctcttgca agtcaagtca gagcctctta gatagtgatg gaaagacata tttgaattgg  120
ttgttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                           336

SEQ ID NO: 6              moltype = AA  length = 8
FEATURE                   Location/Qualifiers
source                    1..8
                          mol_type = protein
                          organism = Mus musculus
SEQUENCE: 6
GFTFSSYV                                                              8

SEQ ID NO: 7              moltype = AA  length = 7
FEATURE                   Location/Qualifiers
source                    1..7
                          mol_type = protein
                          organism = Mus musculus
SEQUENCE: 7
ISSGGST                                                               7

SEQ ID NO: 8              moltype = AA  length = 10
FEATURE                   Location/Qualifiers
source                    1..10
```

-continued

```
                         mol_type = protein
                         organism = Mus musculus
SEQUENCE: 8
LRGQDYGAAY                                                           10

SEQ ID NO: 9             moltype = AA   length = 11
FEATURE                  Location/Qualifiers
source                   1..11
                         mol_type = protein
                         organism = Mus musculus
SEQUENCE: 9
QSLLDSDGKT Y                                                         11

SEQ ID NO: 10            moltype =    length =
SEQUENCE: 10
000

SEQ ID NO: 11            moltype = AA   length = 9
FEATURE                  Location/Qualifiers
source                   1..9
                         mol_type = protein
                         organism = Mus musculus
SEQUENCE: 11
WQGTHFPQT                                                            9

SEQ ID NO: 12            moltype = AA   length = 123
FEATURE                  Location/Qualifiers
source                   1..123
                         mol_type = protein
                         organism = Mus musculus
SEQUENCE: 12
EVQLQQSGTV LARPGASVKM SCKASGYSFT SYWMHWVKQR PGQGLEWIGA IYPGNSDTSY    60
NQKFKGKAKL TAVTSASTAY MELSCLTNED SAVFYCTRSQ FYSGSSEDAM DYWGQGTSVT    120
VSS                                                                  123

SEQ ID NO: 13            moltype = DNA   length = 369
FEATURE                  Location/Qualifiers
source                   1..369
                         mol_type = other DNA
                         organism = Mus musculus
SEQUENCE: 13
gaggttcagc tccagcagtc tgggactgtg ctggcaaggc ctggggcttc cgtgaagatg    60
tcctgcaagg cttctggcta cagctttacc agctactgga tgcactgggt aaaacagagg    120
cctggacagg gtctagaatg gattggtgct atttatcctg gaaatagtga tactagttac    180
aaccagaagt tcaagggcaa ggccaaactg actgcagtca catccgccag cactgcctac    240
atggagctca gctgcctgac aaatgaggac tctgcggtct tttactgtac aagatcccaa    300
ttttactccg gtagtagcga ggatgctatg gactactggg gtcaaggaac ctcagtcacc    360
gtctcctca                                                            369

SEQ ID NO: 14            moltype = AA   length = 112
FEATURE                  Location/Qualifiers
source                   1..112
                         mol_type = protein
                         organism = Mus musculus
SEQUENCE: 14
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YFCFQGSHVP WTFGGGTKLE IK            112

SEQ ID NO: 15            moltype = DNA   length = 336
FEATURE                  Location/Qualifiers
source                   1..336
                         mol_type = other DNA
                         organism = Mus musculus
SEQUENCE: 15
gatgttttga tgacccaaac tccactctcc ctgcctgtca gtcttggaga tcaagcctcc    60
atctcttgca gatctagtca gagcattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct tcaaggttc acatgttccg     300
tggacgttcg gtggaggcac caagctggaa atcaaa                              336

SEQ ID NO: 16            moltype = AA   length = 8
FEATURE                  Location/Qualifiers
source                   1..8
                         mol_type = protein
                         organism = Mus musculus
SEQUENCE: 16
GYSFTSYW                                                             8
```

-continued

```
SEQ ID NO: 17           moltype = AA  length = 8
FEATURE                 Location/Qualifiers
source                  1..8
                        mol_type = protein
                        organism = Mus musculus
SEQUENCE: 17
IYPGNSDT                                                        8

SEQ ID NO: 18           moltype = AA  length = 16
FEATURE                 Location/Qualifiers
source                  1..16
                        mol_type = protein
                        organism = Mus musculus
SEQUENCE: 18
TRSQFYSGSS EDAMDY                                               16

SEQ ID NO: 19           moltype = AA  length = 11
FEATURE                 Location/Qualifiers
source                  1..11
                        mol_type = protein
                        organism = Mus musculus
SEQUENCE: 19
QSIVHSNGNT Y                                                    11

SEQ ID NO: 20           moltype =   length =
SEQUENCE: 20
000

SEQ ID NO: 21           moltype = AA  length = 9
FEATURE                 Location/Qualifiers
source                  1..9
                        mol_type = protein
                        organism = Mus musculus
SEQUENCE: 21
FQGSHVPWT                                                       9

SEQ ID NO: 22           moltype = AA  length = 118
FEATURE                 Location/Qualifiers
source                  1..118
                        mol_type = protein
                        organism = Mus musculus
SEQUENCE: 22
QIQLVQSGPE LKKPGETVKI SCKASGYTFT NYGMNWLKQA PGKGLKWMGW INTNTGEPTY 60
AEEFKGRFAF SLETSASTAY LQINNLKNED TATYFCARKD YRYWFAYWGQ GTLVTVSA   118

SEQ ID NO: 23           moltype = DNA  length = 354
FEATURE                 Location/Qualifiers
source                  1..354
                        mol_type = other DNA
                        organism = Mus musculus
SEQUENCE: 23
cagatccagt tggtgcagtc tggacctgag ctgaagaagc ctggagagac agtcaagatc 60
tcctgcaagg cttctgggta taccttcaca aactatggaa tgaactggct gaagcaggct 120
ccaggaaagg gtttaaagtg gatgggctgg ataaacacca acactggaga gccaacatat 180
gctgaagagt tcaagggacg gtttgccttc tctttggaaa cctctgccag cactgcctat 240
ttgcagatca caacctcaa aaatgaggac acggctacat atttctgtgc aagaaaggac 300
tataggtact ggtttgctta ctggggccaa gggactctgg tcactgtctc tgca       354

SEQ ID NO: 24           moltype = AA  length = 112
FEATURE                 Location/Qualifiers
source                  1..112
                        mol_type = protein
                        organism = Mus musculus
SEQUENCE: 24
DVLMTQTPLS LPVSLGDQAS ISCRSSQSIV HSNGNTYLEW YLQKPGQSPK LLIYKVSNRF 60
SGVPDRFSGS GSGTDFTLKI SRVEAEDLGV YYCFQGSHVP FTFGSGTKLE IK          112

SEQ ID NO: 25           moltype = DNA  length = 336
FEATURE                 Location/Qualifiers
source                  1..336
                        mol_type = other DNA
                        organism = Mus musculus
SEQUENCE: 25
gatgttttga tgacccaaac tccactctcc ctgcctgtca gtcttggaga tcaagcctcc 60
atctcttgca gatctagtca gagcattgta catagtaatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttcca 300
ttcacgttcg gctcggggac aaagttggaa ataaaa                          336
```

-continued

```
SEQ ID NO: 26          moltype = AA  length = 8
FEATURE                Location/Qualifiers
source                 1..8
                       mol_type = protein
                       organism = Mus musculus
SEQUENCE: 26
GYTFTNYG                                                        8

SEQ ID NO: 27          moltype = AA  length = 8
FEATURE                Location/Qualifiers
source                 1..8
                       mol_type = protein
                       organism = Mus musculus
SEQUENCE: 27
INTNTGEP                                                        8

SEQ ID NO: 28          moltype = AA  length = 11
FEATURE                Location/Qualifiers
source                 1..11
                       mol_type = protein
                       organism = Mus musculus
SEQUENCE: 28
ARKDYRYWFA Y                                                    11

SEQ ID NO: 29          moltype = AA  length = 11
FEATURE                Location/Qualifiers
source                 1..11
                       mol_type = protein
                       organism = Mus musculus
SEQUENCE: 29
QSIVHSNGNT Y                                                    11

SEQ ID NO: 30          moltype =    length =
SEQUENCE: 30
000

SEQ ID NO: 31          moltype = AA  length = 9
FEATURE                Location/Qualifiers
source                 1..9
                       mol_type = protein
                       organism = Mus musculus
SEQUENCE: 31
FQGSHVPFT                                                       9
```

What is claimed is:

1. A method of inhibiting *Pseudomonas aeruginosa* biofilm formation in an animal or a human subject in need thereof, the method comprising administering to the subject a therapeutically effective amount of one or more antibodies targeting a CoaB protein of Pf4 bacteriophage or an antigenic fragment thereof, wherein the one or more antibodies comprises:

a heavy chain variable region comprising: (1) the CDR-H1 comprising the amino acid sequence of GFTFSSYV (SEQ ID NO: 6); (2) the CDR-H2 comprising the amino acid sequence of ISSGGST (SEQ ID NO: 7); and (3) the CDR-H3 comprising the amino acid sequence of LRGQDYGAAY (SEQ ID NO: 8) and a light chain variable region comprising: (1) the CDR-L1 comprising the amino acid sequence of QSLL-DSDGKTY (SEQ ID NO: 9); (2) the CDR-L2 comprising the amino acid sequence of LVS (SEQ ID NO: 10); and (3) the CDR-L3 comprising the amino acid sequence of WQGTHFPQT (SEQ ID NO: 11);

a heavy chain variable region comprising: (1) the CDR-H1 comprising the amino acid sequence of GYSFT-SYW (SEQ ID NO: 16); (2) the CDR-H2 comprising the amino acid sequence of IYPGNSDT (SEQ ID NO: 17); and (3) the CDR-H3 comprising the amino acid sequence of TRSQFYSGSSEDAMDY (SEQ ID NO: 18) and a light chain variable region comprising: (1) the CDR-L1 comprising the amino acid sequence of QSIVHSNG-NTY (SEQ ID NO: 19); (2) the CDR-L2 comprising the amino acid sequence of KVS (SEQ ID NO: 20); and (3) the CDR-L3 comprising the amino acid sequence of FQGSHVPWT (SEQ ID NO: 21);

a heavy chain variable region comprising: (1) the CDR-H1 comprising the amino acid sequence of GYTFTNYG (SEQ ID NO: 26); (2) the CDR-H2 comprising the amino acid sequence of INTNTGEP (SEQ ID NO: 27); and (3) the CDR-H3 comprising the amino acid sequence of ARKDYRYWFAY (SEQ ID NO: 28) and a light chain variable region comprising: (1) the CDR-L1 comprising the amino acid sequence of QSIVHSNG-NTY (SEQ ID NO: 29); (2) the CDR-L2 comprising the amino acid sequence of KVS (SEQ ID NO: 30); and (3) the CDR-L3 comprising the amino acid sequence of FQGSHVPFT (SEQ ID NO: 31).

2. The method of claim 1, wherein the animal or the human subject is suffering from cystic fibrosis, burns, chronic wound, chronic rhinosinusitis, ventilator-associated pneumonia, catheter-associated urinary tract infections, septic shock, or gastrointestinal infections caused by *Pseudomonas aeruginosa.*

* * * * *